US008067110B2

(12) United States Patent
Rakow et al.

(10) Patent No.: US 8,067,110 B2
(45) Date of Patent: Nov. 29, 2011

(54) ORGANIC VAPOR SORBENT PROTECTIVE DEVICE WITH THIN-FILM INDICATOR

(75) Inventors: Neal A. Rakow, Woodbury, MN (US); James P. Mathers, Woodbury, MN (US); Jun-Ying Zhang, St. Paul, MN (US); Dora M. Paolucci, St. Paul, MN (US); Richard J. Poirier, White Bear Lake, MN (US); Moses M. David, Woodbury, MN (US); John E. Trend, St. Paul, MN (US); Michael S. Wendland, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 940 days.

(21) Appl. No.: 11/530,614

(22) Filed: Sep. 11, 2006

(65) Prior Publication Data
US 2008/0063575 A1 Mar. 13, 2008

(51) Int. Cl.
*A61L 2/28* (2006.01)
*A61M 16/00* (2006.01)
(52) U.S. Cl. ............ 429/119; 422/68.1; 422/82.05; 422/83; 422/87; 422/88; 422/200.24
(58) Field of Classification Search ............ 128/200.24–207.18; 422/55–60, 422/68.1, 82.05, 83–88
See application file for complete search history.

(56) References Cited

U.S. PATENT DOCUMENTS

| | | |
|---|---|---|
| 1,537,519 A | 5/1925 | Yablick |
| 3,966,440 A | 6/1976 | Roberts |
| 3,971,373 A | 7/1976 | Braun et al. |
| 4,146,887 A | 3/1979 | Magnante |
| 4,153,661 A | 5/1979 | Ree et al. |
| 4,154,586 A | 5/1979 | Jones et al. |
| 4,155,358 A | 5/1979 | McAllister et al. |
| 4,208,194 A | 6/1980 | Nelson |
| 4,326,514 A | 4/1982 | Eian |
| 4,421,719 A | 12/1983 | Burleigh |

(Continued)

FOREIGN PATENT DOCUMENTS
DE 10255463 6/2004
(Continued)

OTHER PUBLICATIONS

"Macromolecules", 2001, vol. 34, pp. 8792-8801.

(Continued)

*Primary Examiner* — In Suk Bullock
*Assistant Examiner* — Robert Eom
(74) *Attorney, Agent, or Firm* — Karl G. Hanson

(57) ABSTRACT

A sorbent media protective device includes an enclosure having a gas inlet, gas outlet and a thin-film multilayer indicator. The thin-film multilayer indicator is proximate sorbent media that can sorb a vapor of interest flowing from the gas inlet towards the gas outlet. The indicator includes a porous detection layer whose optical thickness changes in the presence of the vapor, located between a semireflective layer and a reflective layer permeable to the vapor. With equilibration at the applied vapor concentration between at least a portion of the media and the vapor, the vapor can pass through the reflective layer into the detection layer and change the detection layer optical thickness sufficiently to cause a visibly discernible change in the indicator appearance if viewed through the semireflective layer.

44 Claims, 9 Drawing Sheets

U.S. PATENT DOCUMENTS

| | | | |
|---|---|---|---|
| 4,530,706 A | 7/1985 | Jones |
| 4,597,942 A | 7/1986 | Meathrel |
| 4,641,524 A | 2/1987 | Tarvin |
| 4,684,380 A | 8/1987 | Leichnitz |
| 4,699,511 A | 10/1987 | Seaver |
| 4,732,480 A | 3/1988 | Fortunato et al. |
| 4,778,987 A | 10/1988 | Saaski et al. |
| 4,834,496 A | 5/1989 | Blyler, Jr. et al. |
| 4,846,548 A | 7/1989 | Klainer |
| 4,847,594 A | 7/1989 | Stetter |
| 4,940,328 A | 7/1990 | Hartman |
| 4,945,230 A | 7/1990 | Saaski et al. |
| 4,948,639 A | 8/1990 | Brooker et al. |
| 5,250,095 A | 10/1993 | Sigel, Jr. et al. |
| 5,280,548 A | 1/1994 | Atwater et al. |
| 5,297,544 A | 3/1994 | May et al. |
| 5,308,771 A | 5/1994 | Zhou et al. |
| 5,323,774 A | 6/1994 | Fehlauer |
| 5,337,376 A | 8/1994 | Ravetti et al. |
| 5,338,415 A | 8/1994 | Sailor et al. |
| 5,376,554 A | 12/1994 | Vo-Dinh |
| 5,436,167 A | 7/1995 | Robillard |
| H1470 H | 8/1995 | Ewing et al. |
| 5,453,624 A | 9/1995 | Sailor et al. |
| 5,493,730 A | 2/1996 | Vo-Dinh |
| 5,512,882 A | 4/1996 | Stetter et al. |
| 5,611,998 A | 3/1997 | Aussenegg et al. |
| 5,659,296 A | 8/1997 | Debe et al. |
| 5,666,949 A | 9/1997 | Debe et al. |
| 5,685,969 A | 11/1997 | Hoenig et al. |
| 5,699,188 A | 12/1997 | Gilbert et al. |
| 5,783,836 A | 7/1998 | Lu et al. |
| 5,828,798 A | 10/1998 | Hopenfeld |
| 5,858,457 A | 1/1999 | Brinker et al. |
| 5,882,774 A | 3/1999 | Jonza et al. |
| 6,007,904 A | 12/1999 | Schwotzer et al. |
| 6,010,751 A | 1/2000 | Shaw et al. |
| 6,049,419 A | 4/2000 | Wheatley et al. |
| 6,130,748 A | 10/2000 | Krüger et al. |
| 6,248,539 B1 | 6/2001 | Ghadiri et al. |
| 6,278,106 B1 | 8/2001 | Muto et al. |
| 6,312,793 B1 | 11/2001 | Grill et al. |
| 6,375,725 B1 | 4/2002 | Bernard et al. |
| 6,422,059 B1 | 7/2002 | Greenbank et al. |
| 6,497,756 B1 | 12/2002 | Curado et al. |
| 6,573,305 B1 | 6/2003 | Thunhorst et al. |
| 6,590,665 B2 | 7/2003 | Painchaud et al. |
| 6,701,864 B2 | 3/2004 | Watson, Jr. et al. |
| 2004/0062682 A1 | 4/2004 | Rakow et al. |
| 2004/0135684 A1 | 7/2004 | Steinthal et al. |
| 2004/0184948 A1 | 9/2004 | Rakow et al. |
| 2004/0189982 A1 | 9/2004 | Galarneau et al. |
| 2004/0204915 A1 | 10/2004 | Steinthal et al. |
| 2004/0223876 A1 | 11/2004 | Kirollos et al. |
| 2005/0188749 A1 | 9/2005 | Custer et al. |
| 2006/0096911 A1 | 5/2006 | Brey et al. |
| 2006/0163744 A1* | 7/2006 | Vanheusden et al. ......... 257/773 |

FOREIGN PATENT DOCUMENTS

| | | |
|---|---|---|
| WO | WOX 94/03774 | 2/1994 |
| WO | WO 96/12524 | 5/1996 |
| WO | WO 97/01778 | 1/1997 |
| WO | WO 2004/057314 A2 | 7/2004 |
| WO | WO 2005/012397 A2 | 2/2005 |
| WO | WO 2005/111588 A1 | 11/2005 |

OTHER PUBLICATIONS

"Science", 1999, vol. 283, p. 520.
Ogawa et al., *Chem. Commun.* pp. 1149-1150 (1996).
Kresge et al., *Nature*, vol. 359, pp. 710-712 (1992).
Jia et al., *Chemistry Letters*, vol. 33(2), pp. 202-203 (2004).
Wei et al, *Adv. Mater*.1998, vol. 10, p. 313 (1998).
"Polymers of intrinsic microporosity (PIMs): robust, solution-processable, organic microporous materials," Budd et al., *Chem. Commun.*, 2004, pp. 230-231.
Budd et al., *J. Mater. Chem.*, 2005, 15, pp. 1977-1986.
McKeown et al., *Chem. Eur. J.* 2005, 11, No. 9, 2610-2620.
V. A. Davankov and P. Tsyurupa, *Pure and Appl. Chem.*, vol. 61, pp. 1881-1889 (1989).
L. D. Belyakova, T. I. Schevchenko, V. A. Davankov and M.P. Tsyurupa, *Adv. in Colloid and Interface Sci.* vol. 25, pp. 249-66, (1986)).
Budd et al. in *Advanced Materials*, 2004, vol. 16, No. 5, pp. 456-459.
Liu, Rong, et al., *Novel Porous Silicon Vapor Sensor Based on Polarization interferometry*, Sensors and Actuators B, vol. 87, No. 1, Nov. 15, 2002, pp. 58-62.

* cited by examiner

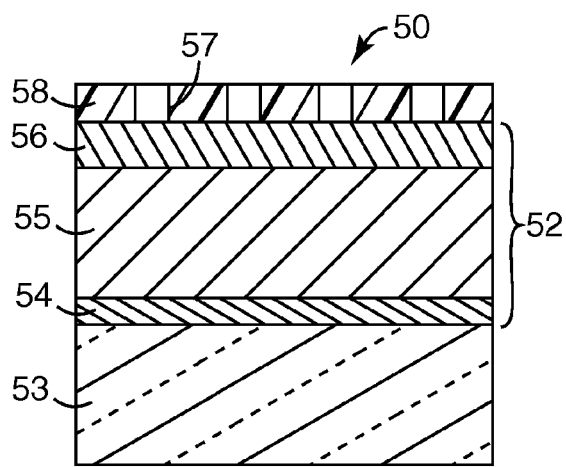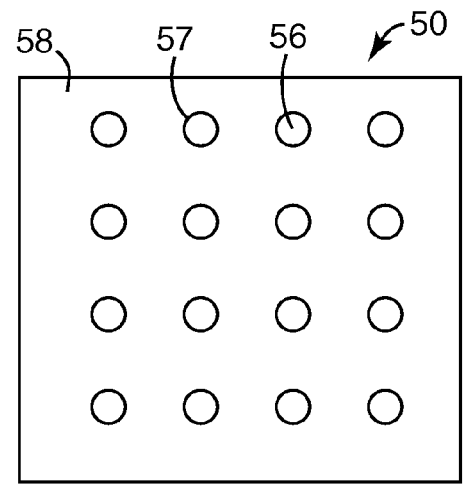
*Fig. 5a* *Fig. 5b*
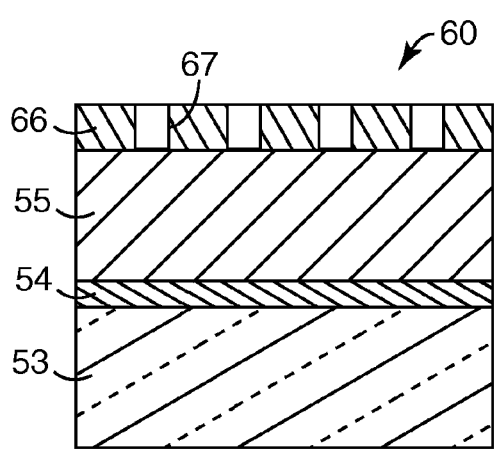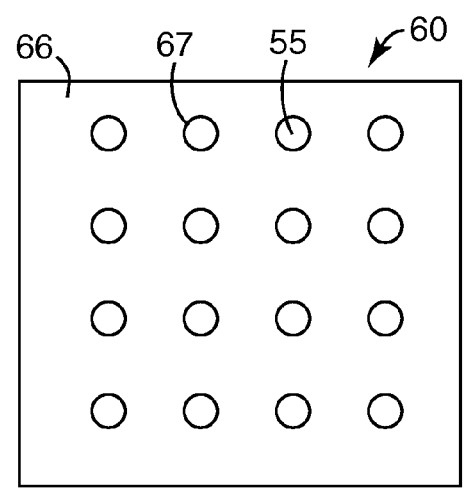
*Fig. 6a* *Fig. 6b*
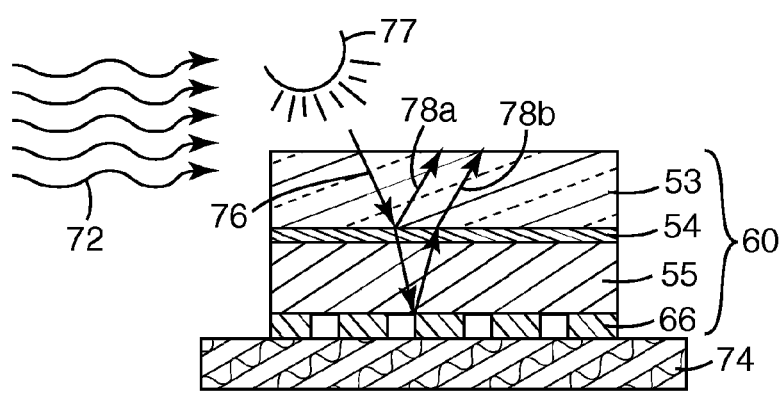
*Fig. 7*

ORGANIC VAPOR SORBENT PROTECTIVE DEVICE WITH THIN-FILM INDICATOR

This invention relates to organic vapor sorbent protective devices.

BACKGROUND

Various chemical, optical or electronic indicators have been proposed for warning users of disposable personal respirators, powered air purifying respirators, haz-mat suits and other protective devices of the presence of undesired materials. For example, an end-of-service-life indicator ("ESLI") can warn that a filter element in such a device may be approaching saturation or may be ineffective against a particular material. Patents and applications relating to personal protection or respiratory protection (and in some instances to sensors or indicators in general or to ESLIs in particular) include U.S. Pat. No. 1,537,519 (Yablick), U.S. Pat No. 3,966,440 (Roberts), U.S. Pat. No. 4,146,887 (Magnante), U.S. Pat. No. 4,154,586 (Jones et al.), U.S. Pat. No. 4,155,358 (McAllister et al.), U.S. Pat. No. 4,326,514 (Eian), U.S. Pat. No. 4,421,719 (Burleigh), U.S. Pat. No. 4,530,706 (Jones), U.S. Pat. No. 4,597,942 (Meathrel), U.S. Pat. No. 4,684,380 (Leichnitz), U.S. Pat. No. 4,847,594 (Stetter), U.S. Pat. No. 5,297,544 (May et al.), U.S. Pat. No. 5,323,774 (Fehlauer), U.S. Pat. No. 5,376,554 (Vo-Dinh), U.S. Pat. No. 5,512,882 (Stetter et al.), U.S. Pat. No. 5,666,949 (Debe et al. '949), U.S. Pat. No. 5,659,296 (Debe et al. '296), U.S. Pat. No. 6,375,725B1 (Bernard et al.), U.S. Pat. No. 6,497,756B1 (Curado et al.) and U.S Pat. No. 6,701,864 B2 (Watson, Jr. et al.); US. Patent Application Publication Nos. US 2004/0135684 A1 (Steinthal et al.), US 2004/0189982 A1 (Galarneau et al.), US 2004/0223876 A1 (Kirollos et al.) and US 2005/0188749 A1 (Custer et al.); and PCT Published Patent Application No. WO 2004/057314 A2.

SUMMARY OF THE INVENTION

Other patents and patent applications relating to sensors or indicators but not to ESLIs include U.S. Pat. No. 5,611,998 (Aussenegg et al.), U.S Pat. No. 5,783,836 (Liu et al.), U.S. Pat. No. 6,007,904 (Schwotzer et al.), U.S. Pat. No. 6,130,748 (Krüger et al.) and U.S. Pat. No. 6,248,539 (Ghadiri et al.); U.S. Patent Application Publication No. US 2004/0184948 A1 (Rakow et al.); and US Statutory Invention Registration No. H1470 (Ewing et al.).

Some of the above-mentioned sensors or indicators have drawbacks such as a requirement for electronic instrumentation and electrical power, an undesirably complex or expensive design, insufficient sensitivity or sensitivity to only one or to only a few substances. Also, some sensors or indicators have been disclosed as being usable for detecting liquids or vapors, but have not been disclosed to be useful for detecting the extent of sorption by a solid.

The invention provides in one aspect a protective device that comprises an enclosure including a gas inlet, gas outlet and a thin-film multilayer indicator, wherein:
  A) the enclosure contains sorbent media that can sorb a vapor of interest flowing from the inlet towards the outlet;
  B) the thin-film multilayer indicator comprises:
    i) a porous detection layer whose optical thickness changes in the presence of the vapor, located between
    ii) a semireflective layer viewable from outside the enclosure and not permeated by the vapor, and
    iii) a reflective layer permeable to the vapor; and
  C) the reflective layer is in sufficient proximity to the media such that with equilibration at the applied vapor concentration between at least a portion of the media and the vapor, the vapor can pass through the reflective layer into the detection layer and change the detection layer optical thickness sufficiently to cause a visibly discernible change in the indicator appearance as viewed through the semireflective layer.

The invention provides in another aspect a process for making a protective device, which process comprises:
  A) providing an enclosure including:
    i) a space for containing sorbent media that will sorb a vapor of interest flowing through the enclosure; and
    ii) a thin-film multilayer indicator comprising:
      a) a porous detection layer whose optical thickness will change in the presence of the vapor, located between
      b) a semireflective layer viewable from outside the enclosure and not permeated by the vapor, and
      c) a reflective layer permeable to the vapor;
  B) placing the media in the enclosure in sufficient proximity to the reflective layer such that with equilibration at the applied vapor concentration between at least a portion of the media and the vapor, the vapor can pass through the reflective layer into the detection layer and change the detection layer optical thickness sufficiently to cause a visibly discernible change in the indicator appearance as viewed through the semireflective layer; and
  C) sealing the enclosure.

The disclosed thin-film multilayer indicator is permeable from the reflective layer side and can provide a discernable calorimetric change from the semireflective layer side. This enables the detection of solvent vapor while the indicator is in contact with or near solid sorbent media such as the porous carbon media often employed in disposable personal respirator cartridges. The indicator can provide a vivid, readily visibly discernible change in indicator appearance (e.g., a calorimetric change) when the media becomes equilibrated with the vapor, and without requiring a powered light source, optical detector or spectral analyzer. The indicator can provide advantages including low cost, ease of use, robustness, and broad spectrum sensitivity with respect to a variety of vapors of interest.

These and other aspects of the invention will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

FIG. 5a and FIG. 5b are schematic side sectional and top views, respectively, of a thin-film multilayer indicator precursor coated with a perforated photoresist.

FIG. 6a and FIG. 6b are schematic side sectional and top views, respectively, of the FIG. 5a and FIG. 5b precursor after the aluminum reflective layer has been perforated by etching and the photoresist removed.

FIG. 7 through FIG. 9 are schematic side sectional views of the disclosed thin-film multilayer indicator mounted in proximity to various sorbent media;

DETAILED DESCRIPTION

Figure 1:
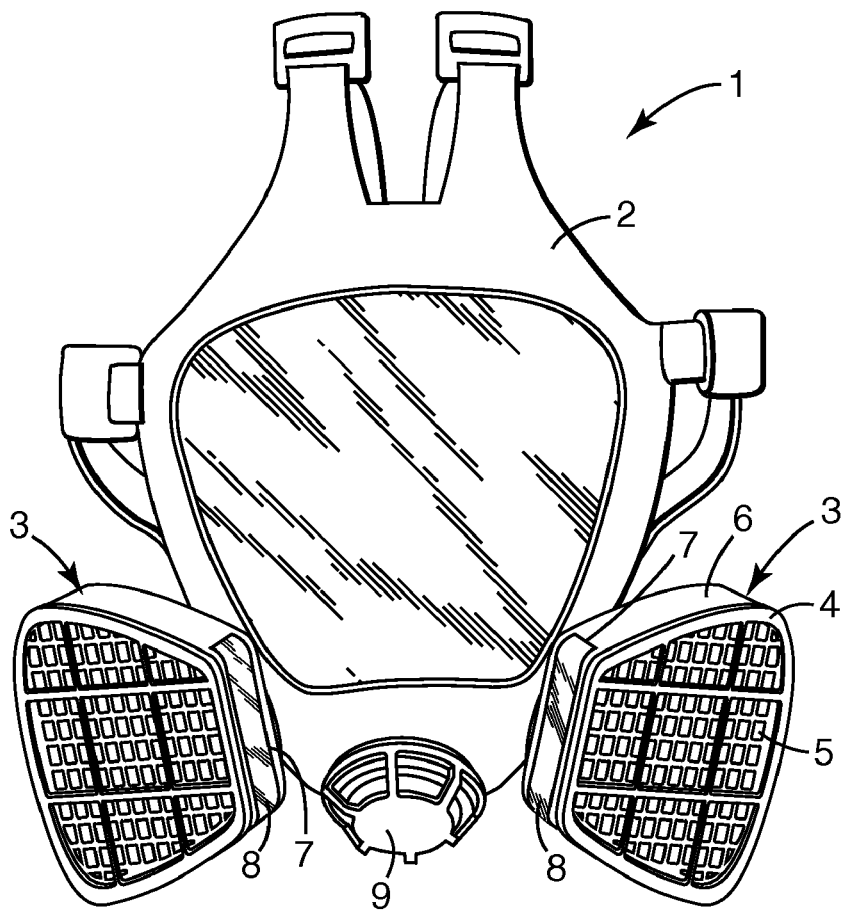
FIG. 1 is a perspective view of a respirator with replaceable sorbent cartridges equipped with a thin-film multilayer end of service life indicator.

The terms set forth below are defined as follows:

"Vapor of interest" means an organic or inorganic vapor whose removal from ambient air (e.g., breathing air) is desired.

"Analyte" means the specific vapor of interest or other component that is being detected, e.g., in a chemical or biochemical analysis.

"Optically-responsive" when used with respect to an article or a detection layer means that the article or detection layer exhibits a responsive change in a detectible optical property when an analyte is present, such as a change in optical thickness (viz., physical thickness or refractive index), reflectivity, phase shift, polarization, birefringence or light transmission.

"Enclosure" means a cartridge, capsule, pouch, containment, housing or other structure in which sorbent media can be emplaced, sealed if need be for storage or shipment, later unsealed if need be for installation and use, and thereafter employed to sorb a vapor of interest.

"Reflective" when used with respect to a layer means that the layer reflects visible light.

"Semireflective layer" means a first reflective layer, which in reference to a second reflective layer, has lower reflectivity and greater light transmission than the second reflective layer and which may, for example, be used in spaced relation to the second reflective layer to provide interference coloration.

"Vapor-permeable" when used with respect to a reflective layer one side of which is in fluid communication with a porous detection layer means that if the other side of the reflective layer is exposed to an air stream containing 1000 ppm styrene monomer vapor flowing at 20 liters/min for 15 minutes, sufficient styrene monomer will pass through the reflective layer so that an optically-responsive change takes place in the detection layer.

"Porous" when used with respect to a material means that the material contains a connected network of pores (which may, for example, be openings, interstitial spaces or other channels) throughout its volume.

"Size" when used with respect to a pore means the pore diameter for a pore having a circular cross section, or the length of the longest cross-sectional chord that may be constructed across a pore having a non-circular cross-section.

"Microporous" when used with respect to a material means that the material is porous with an average pore size of about 0.3 to 100 nanometers.

"Continuous" when used with respect to a layer of a material means that the layer is non-porous and is not vapor-permeable.

"Semicontinuous" when used with respect to a layer of a material means that the layer is porous and vapor-permeable.

"Discontinuous" when used with respect to a layer of a material means that the layer has at least two separate and distinct islands of the material within a given plane with empty space therebetween, or at least two separate and distinct empty spaces (lakes) within a given plane with the material therebetween, and that the layer is vapor-permeable.

The disclosed devices may be used to detect a variety of vapors of interest. Representative vapors of interest include water vapor, gases, and volatile organic chemical compounds. Representative organic chemical compounds include substituted or unsubstituted carbon compounds including alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile.

Referring to FIG. 1, a personal respirator 1 includes a face mask 2 on which is mounted a pair of replaceable air purifying respirator cartridges 3. The cartridges 3 each serve as enclosures for a sorbent material (e.g., activated carbon) not shown in FIG. 1. The front cover 4 of each cartridge 3 includes a plurality of openings 5 that serve as gas inlets, permitting ambient air from the external environment to flow into cartridge 3, through the sorbent material and thence through a passage (not labeled in FIG. 1) that serves as a gas outlet from cartridge 3 and an inlet to face mask 2. The sidewall 6 in each cartridge 3 includes a transparent viewing port 7 through which a wearer of face mask 2 can see thin-film multilayer indicator 8. Each indicator 8 may wrap around one or more curved regions in the cartridge 3 to provide improved visibility from a variety of viewing angles and to permit the cartridges 3 to be mounted on either side of respirator 1. Indicator 8 is optically responsive, undergoing a visibly discernible colorimetric change when the sorbent material becomes equilibrated with the vapor at the conditions of exposure, thus aiding the wearer in recognizing that it is time to replace the cartridge or cartridges 3. Exhaled air exits respirator 1 through exhalation valve 9. The indicator may be used in a variety of respiratory protective devices. For example, the indicator may also be deployed in a single cartridge respirator or a powered air-purifying respirator.

Figure 2:
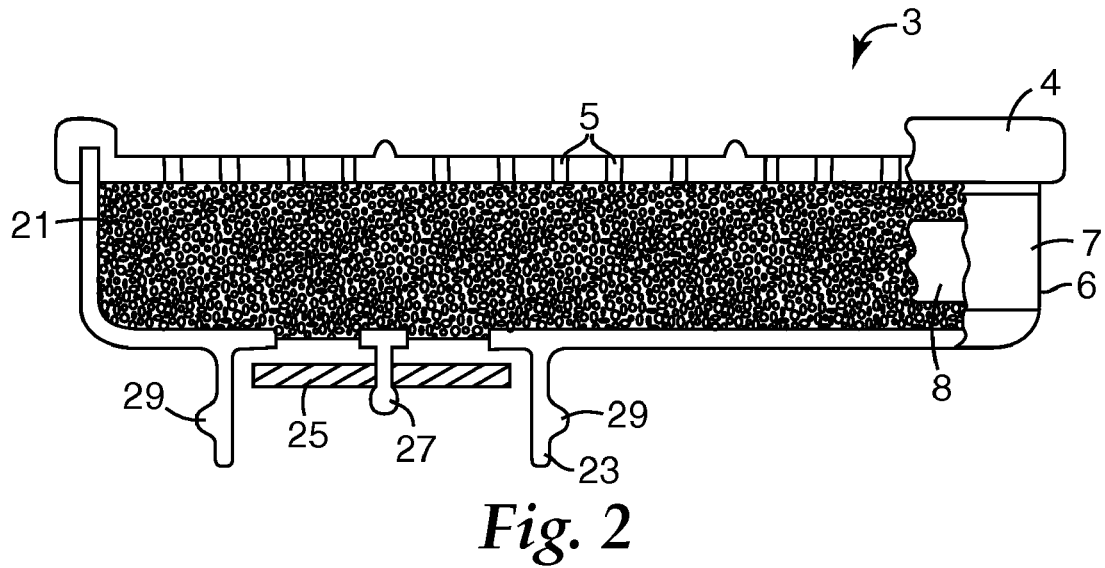
FIG. 2 is a side view, partially in section, of a carbon-filled replaceable cartridge for use in the respirator of FIG. 1.

FIG. 2 is a side view, partially in section, of respirator cartridge 3. If desired, the openings 5 could be sealed until use using for example a removable cover (not shown in FIG. 1 and FIG. 2) that would be removed before use. A bed of sorbent material 21 absorbs or adsorbs vapors of interest passing from the openings 5 to outlet 23. One-way inhalation valve 25 mounted on post 27 prevents exhaled air from entering cartridge 3. A threaded or preferably bayoneted connector or connectors 29 can be used to removably couple cartridge 3 to mask 2. Sidewall 6 includes a transparent viewing port 7 over thin-film multilayer indicator 8. Port 7 permits ambient light to pass into indicator 8 through a semireflective layer (not labeled in FIG. 2) in indicator 8 located adjacent viewing port 7. If desired, a removable or replaceable shield or other covering (not shown in FIG. 2) may optionally be used to protect port 7 from paint or foam overspray, dust, or other obscuration. The ambient light entering port 7 and indicator 8 is returned through viewing port 7 by a vapor-permeable reflective layer (not labeled in FIG. 2) in indicator 8 located adjacent sorbent material 21. The cartridges 3 would be removed and replaced with fresh cartridges 3 when a visibly discernible change in the appearance of indicator 8 (e.g., a change in color such as from green to red, an appearance or disappearance of color such as from white or black to colored or from colored to white or black, or a change from white to black or from black to white) indicates that the sorbent material 21 underneath indicator 8 has become equilibrated with the vapor at the conditions of exposure. By configuring indicator 8 so that it covers the full length of the vapor flow path, an appearance change (e.g., a color change) "front" would advance with the flow of vapor through the sorbent material 21 and past indicator 8. The advancing appearance change front would indicate the remaining service life for cartridge 3 (like a bar gauge or fuel gauge) rather than just the end of service life, especially where appropriate care is taken to design cartridge 3 so that its remaining lifetime is linearly proportional to the spatial vapor front penetration past indicator 8. Alternatively, indicator 8 could be placed toward the end of the flow path only so as to give warning only at the desired remaining service life percentage. Indicator 8 or viewing port 7 may if desired include a pattern or reference color to assist in visual discernment of changes in the appearance of indicator 8. As mentioned, appearance changes in indicator 8 could be visibly monitored under ambient lighting. Alternatively, indicator 8 could be illuminated using an external light source such as a light emitting diode (LED) and evaluated using a photodetector mounted on the periphery of cartridge 3 to provide an optoelectronic signal. Whether viewed under ambient light or by using an external light source and photodetector, the breadth of chemical detection could if desired be increased in a variety of ways. For example, a small array of indicators traversing the vapor flow path could be employed. Each indicator could contain different porous detection layer materials (e.g., a silica detection layer, a detection layer applied by plasma-activated chemical vapor deposition ("PCVD"), and a detection layer made from polymers having intrinsic microporosity ("PIMs"), all discussed below). Also, a series of indicators could contain the same detection layer material (e.g., silica) treated using a series of different chemical treatments to provide a range of sorptive properties. Porous silica may, for example, be treated with various alkyl silanes in order to impart a more hydrophobic character to the pores.

Figure 3:
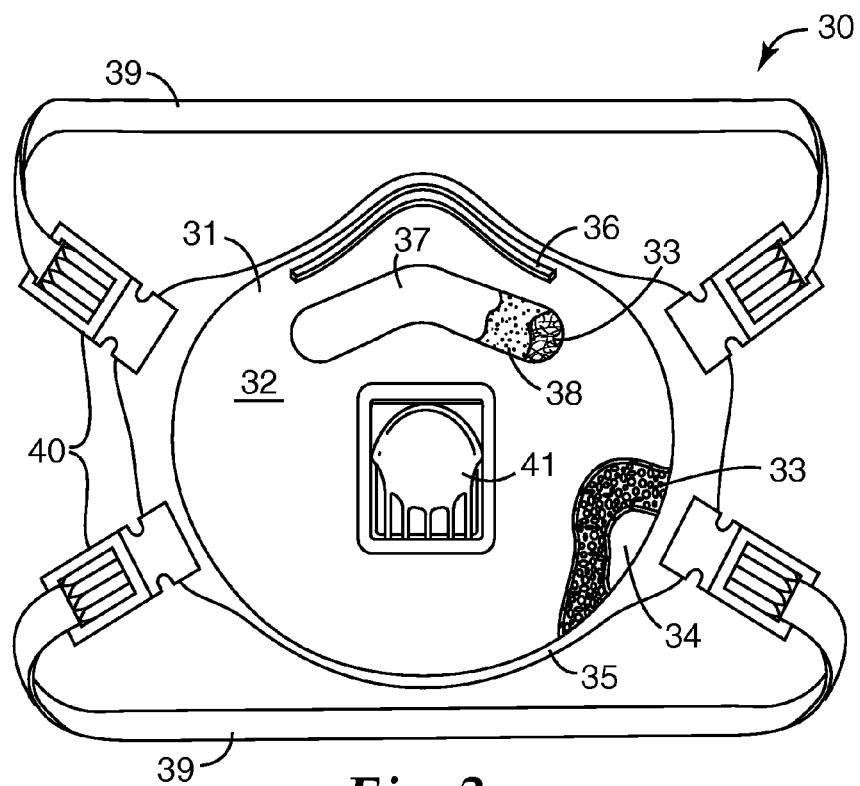
FIG. 3 is a perspective view, partially in section, of a disposable personal respiratory device equipped with a thin-film multilayer end of service life indicator.

FIG. 3 shows a disposable personal respirator 30 in partial cross-section. Device 30 may be for example a disposable mask like that shown in U.S. Pat. No. 6,234,171 B1 (Springett et al.), modified to include a thin-film ESLI. Device 30 has a generally cup-shaped shell or respirator body 31 made from an outer cover web 32, sorbent particles 33 and inner cover web 34. Welded edge 35 holds these layers together and provides a face seal region to reduce leakage past the edge of device 30. Leakage is further reduced by pliable dead-soft metal nose band 36 of a metal such as aluminum. Device 30 includes a transparent viewing port 37 and thin-film multilayer indicator 38 adjacent sorbent particles 33. Device 30 also includes adjustable head and neck straps 39 fastened to device 30 by tabs 40, and exhalation valve 41. Further details regarding the construction of such a respirator will be familiar to those skilled in the art.

Figure 4:
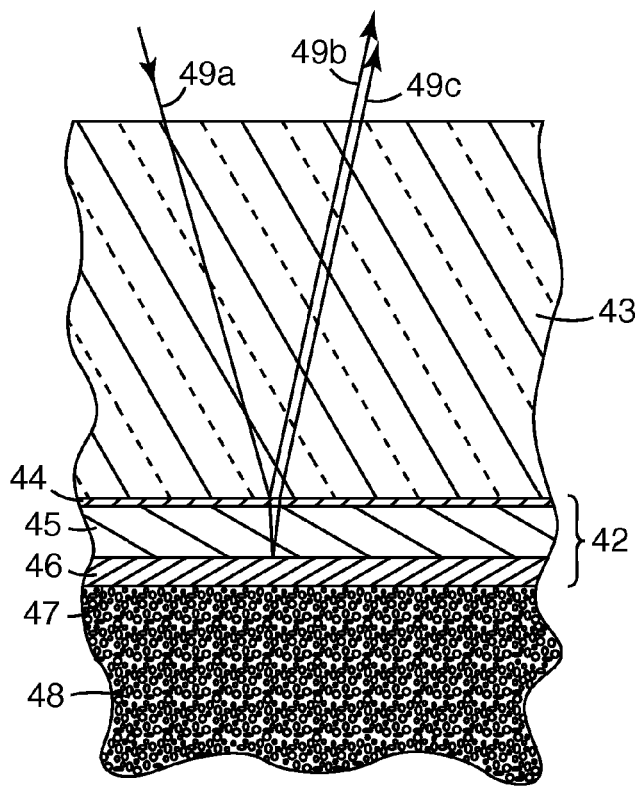
FIG. 4 is a schematic sectional view of a thin-film multilayer indicator.

FIG. 4 shows a schematic view of thin-film multilayer indicator 42 adjacent a transparent substrate 43 and sorbent media 48. Indicator 42 includes semireflective layer 44, porous detection layer 45 and vapor-permeable reflective layer 46. Upon the occurrence of or soon after equilibration at the applied vapor concentration between at least a portion of the media 48 and a vapor of interest, the vapor can pass through pores 47 into detection layer 45. Detection layer 45 is made from a suitable material or made with a suitable structure so that the layer's optical thickness changes (e.g., increases) upon exposure to the vapor of interest. The resulting optical thickness change brings about a visibly perceptible appearance change in indicator 42. The change can be observed by looking at indicator 42 from the outside, viz., through substrate 43. A portion of ambient light represented by ray 49a passes through substrate 43, is reflected from semireflective layer 44 as light ray 49b, travels back through substrate 43, and then passes outside substrate 43. Another portion of ambient light ray 49a passes through substrate 43, semireflective layer 44 and detection layer 45 and is reflected from reflective layer 46 as light ray 49c. Light ray 49c travels back through detection layer 45, semireflective layer 44 and substrate 43, and then passes outside substrate 43. If an appropriate initial or changed thickness has been chosen for detection layer 45, and provided that layers 44 and 46 are sufficiently flat, then interference coloration will be created or destroyed within indicator 42 and light rays like rays 49b and 49c, and a visibly discernible change in the appearance of indicator 42 will be apparent when viewed through semireflective layer 44. Thus external equipment such as a powered light source, optical detector or spectral analysis would not be required to evaluate the condition of indicator 42, although such external equipment may be used if desired.

The disclosed devices may employ a variety of sorbent media. The sorbent media will be capable of sorbing vapors of interest expected to be present under the intended use conditions. The sorbent media desirably is sufficiently porous to permit the ready flow of air or other gases therethrough, and may be in the form of a finely-divided solid (e.g., powder, beads, flakes, granules or agglomerates) or porous solid (e.g., an open-celled foam). Preferred sorbent media materials include activated carbon; alumina and other metal oxides that can remove a vapor of interest by adsorption; clay and other minerals treated with acidic solutions such as acetic acid or alkaline solutions such as aqueous sodium hydroxide; molecular sieves and other zeolites; other inorganic sorbents such as silica; and organic sorbents including hyper-crosslinked systems, such as the highly crosslinked styrenic polymers known as "Styrosorbs" (as described for example in V. A. Davankov and P. Tsyurupa, *Pure and Appl. Chem.*, vol. 61, pp. 1881-89 (1989) and in L. D. Belyakova, T. I. Schevchenko, V. A. Davankov and M. P. Tsyurupa, *Adv. in Colloid and Interface Sci.* vol. 25, pp. 249-66, (1986)). Activated carbon and alumina are particularly preferred sorbent media. Mixtures of sorbent media can be employed, e.g., to absorb mixtures of vapors of interest. If in a finely divided form, the sorbent particle size can vary a great deal and usually will be chosen based in part on the intended service conditions. As a general guide, finely-divided sorbent media particles may vary in size from about 4 to about 3000 micrometers average diameter, e.g., from about 30 to about 1500 micrometers average diameter. Mixtures of sorbent media particles having different size ranges can also be employed, (e.g., in a bimodal mixture of sorbent media particles or in a multilayer arrangement employing larger sorbent particles in an upstream layer and smaller sorbent particles in a downstream layer). Sorbent media combined with a suitable binder (e.g., bonded carbon)

or captured on or in a suitable support such as described in U.S. Pat. No. 3,971,373 (Braun et al.), U.S. Pat. No. 4,208,194 (Nelson) and U.S. Pat. No. 4,948,639 (Brooker et al.) and in U.S. Patent Application Publication No. US 2006/0096911 A1 (Brey et al.) may also be employed.

The indicator may be rigid or flexible. Flexible indicators desirably are sufficiently bendable without fracturing so that they can be made using one or more roll processing steps, and if need be bent in use, e.g., around a corner of a sorbent media enclosure as shown in FIG. 1. The indicator may be attached to a filter housing or other support using a variety of techniques, including film or bulk adhesives, mechanical inserts, thermal bonding, ultrasonic welding and combinations thereof.

The substrate is optional, but when present it may be made from a variety of materials capable of providing a suitably transparent support for the thin-film indicator. The substrate may be rigid (e.g., glass) or flexible (e.g., a plastic film that may be handled in one or more roll processing steps). If made of a flexible material such as a suitably transparent plastic, the substrate desirably has sufficiently low vapor permeability so that the vapor(s) of interest will not be transmitted into or out of the detection layer through the semireflective layer. If the substrate is omitted then the semireflective layer should be sufficiently impermeable to discourage or prevent such vapor transmission. A porous substrate may if desired be placed between the reflective layer and the sorbent media. For example, vapors of interest could be allowed to pass from the sorbent media through the permeable substrate and reflective layer and thence into the detection layer.

The semireflective and reflective layers may each be made from a variety of materials that provide diffuse or preferably specular light reflection and which can cooperate when appropriately spaced apart to provide a readily visibly perceptible indicator appearance change. Suitable semireflective and reflective layer materials include metals such as aluminum, chromium, gold, nickel, silicon, silver, palladium, platinum, titanium and alloys containing such metals; metal oxides such as chrome oxide, titanium oxide and aluminum oxide; and the multilayer optical films (including birefringent multilayer optical films) described in U.S. Pat. No. 5,699,188 (Gilbert et al.), U.S. Pat. No. 5,882,774 (Jonza et al.) and U.S. Pat. No. 6,049,419 (Wheatley et al.), and PCT Published Application No. WO 97/01778 (Ouderkirk et al.). The semireflective and reflective layers may be the same or different. Metal nanoparticle coatings (e.g., metal nanoparticle inks) may be employed to form the reflective layer, as described in copending U.S. patent application Ser. No. 11/530,619, filed even date herewith and entitled PERMEABLE NANOPARTICLE REFLECTOR.

The semireflective layer is less reflective than the reflective layer and transmits some incident light. The semireflective layer may, for example, have a physical thickness of about 2 to about 50 nm, light transmission at 500 nm of about 20 to about 80%, and reflectance at 500 nm of about 80 to about 20%. The semireflective layer may itself be impermeable to vapor (and if so desirably is continuous) and optionally coated on or otherwise adjacent to a suitable substrate. The semireflective layer may also be permeable to vapor (and if so may, for example, be discontinuous or semicontinuous) and coated on or otherwise adjacent to a suitably vapor-impermeable substrate. The face of the semireflective layer adjacent the detection layer desirably is flat to within about ±10 nm.

The reflective layer may, for example, have a physical thickness of about 1 to about 500 nm, light transmission at 500 nm of about 0 to about 80%, and reflectance at 500 nm of about 100 to about 20%. The reflective layer preferably is porous, patterned, discontinuous, semicontinuous or otherwise sufficiently permeable so that vapor can pass from the sorbent media through the reflective layer into the detection layer. The desired pores or discontinuities may be achieved through suitable deposition techniques or through appropriate post-deposition processing such as selective etching, reactive ion etching or patterned laser ablation. The reflective layer may also be formed by depositing a vapor-permeable metal nanoparticle layer as described in the above-mentioned copending U.S. patent application Ser. No. 11/530,619 to form a vapor-permeable layer of packed nanoparticles, with pores being provided by interstices between the nanoparticles. If desired, discontinuities may be formed in the reflective layer in the pattern of a shape, letter, symbol, or message. This can cause a discernible pattern to emerge or disappear upon exposure to the vapor(s) of interest. A viewer may find it easier to discern the contrasting color of such a pattern than to discern a calorimetric change in the overall indicator film.

The detection layer mixture may be homogeneous or heterogeneous, and may, for example, be made from a mixture of inorganic components, a mixture of organic components, or a mixture of inorganic and organic components. Detection layers made from a mixture of components may provide improved detection of groups of analytes. The detection layer desirably has a range of pore sizes or a surface area selected to provide vapor sorption characteristics like those of the sorbent media. Suitable porosity can be obtained by using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, e.g., with average pore sizes of about 0.5 to about 20 nm, 0.5 to about 10 nm, or 0.5 to about 5 nm.

Representative inorganic detection layer materials include porous silica, metal oxides, metal nitrides, metal oxynitrides and other inorganic materials that can be formed into transparent and porous layers of appropriate thickness for producing color or a calorimetric change by optical interference. For example, the inorganic detection layer materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection layer material due to its robustness and compatibility with wet etching treatments.

Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers that will be apparent to persons having ordinary skill in the art. The sol-gel mixture may be converted to a silicate and the organic template may be removed to leave a network of micropores within the silica. Representative porous silica materials are described in Ogawa et al., *Chem. Commun.* pp. 1149-1150 (1996), in Kresge et al., *Nature*, Vol. 359, pp. 710-712 (1992), in Jia et al., *Chemistry Letters*, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, *Adv. Mater.* 1998, Vol. 10, p. 313 (1998). Organo-substituted siloxanes or organo-bis-siloxanes may be included in the sol-gel composition to render the micropores more hydrophobic and limit sorption of water vapor. Plasma chemical vapor deposition may also be employed to generate porous inorganic detection materials. This methodology generally involves forming an analyte detection layer by forming a plasma from gaseous precursors, depositing the plasma on a substrate to form an amorphous random covalent network layer, and then heating the amorphous covalent network layer to form a microporous amorphous random covalent network layer. Examples of such materials are described in U.S. Pat. No. 6,312,793 (Grill et al.) and U.S. patent application Ser. No. 11/275,277 filed Dec. 21, 2005 and entitled PLASMA DEPOSITED MICROPOROUS ANALYTE DETECTION LAYER.

Representative organic detection layer materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof. The above-mentioned U.S. Patent Application Publication No. US 2004/0184948 A1 contains an extensive list of such monomers and reference is made thereto for further details. The above-mentioned polymers having intrinsic microporosity (PIMs) provide particularly desirable detection layers. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., *Chem. Commun.*, 2004, pp. 230-231. Additional PIMs are disclosed in Budd et al., *J. Mater. Chem.*, 2005, 15, pp. 1977-1986, in McKeown et al., *Chem. Eur. J.* 2005, 11, No. 9, 2610-2620 and in Published PCT application No. WO 2005/012397 A2 (McKeown et al.).

One or more polymers within an organic detection layer may be at least partially crosslinked. Crosslinking may be desirable in some embodiments because it can increase mechanical stability and sensitivity to certain analytes. Crosslinking can be achieved by incorporating one or more multifunctional monomers into the detection layer, by subjecting the detection layer to, e.g., electron beam or gamma ray treatment, by adding or forming coordination compounds or ionic compounds in the detection layer, or by forming hydrogen bonds in the detection layer. In one exemplary embodiment, crosslinking is carried out in the presence of a porogen which may be subsequently extracted from the crosslinked system to yield a porous detection layer. Suitable porogens include, but are not limited to, inert organic molecules, such as normal alkanes (e.g., decane) or aromatics (e.g., benzene or toluene). Other crosslinked polymers include the above-mentioned highly crosslinked styrenic polymers.

If desired, the detection layer material may be treated to modify its surface properties or adsorption characteristics. A variety of such treatments may be employed, e.g., by exposing the micropores of an inorganic detection layer to a suitable organosilane compound. The detection layer may also or instead be treated with a suitable adhesion promoting material (e.g., a tie layer made of titanium or another suitable metal) to promote adhesion between the semireflective or reflective layer and the detection layer. Such treatments may also be applied to the semireflective or reflective layers to promote adhesion to the detection layer.

For many applications, the detection layer desirably is hydrophobic. This will reduce the chance that water vapor (or liquid water) will cause a change in the detection layer optical thickness and interfere with the detection of an analyte, for example, the detection of organic solvent vapors.

The detection layer may be made from a single layer or from two or more sublayers. The sublayers may have a variety of configurations. For example, they may be stacked or arranged side by side. The sublayers may also be made from different materials selected to absorb different vapors of interest. A layer or one of a set of sublayers may be discontinuous or patterned. The pattern may create or remove a colored image, word or message upon exposure to an analyte, thereby providing an easily identifiable warning for a user. Layer or sublayer patterns may also be formed by providing one or more portions that are reactive to a particular analyte and one or more portions that are non-reactive to the same analyte. A pattern of reactive material may also be deposited on a larger non-reactive sublayer, e.g., by making the patterned layer sufficiently thin so that no difference in optical thickness is apparent until an analyte is absorbed. The thickness of the detection layer may also be patterned, e.g., as described in U.S. Pat. No. 6,010,751 (Shaw et al.). This can permit a pattern to disappear (for example when a thinner portion swells to the same thickness as a thicker portion) or to appear (for example, when a portion shrinks to a lesser thickness than an adjacent portion).

The disclosed devices may include additional layers or elements if desired. For example, a porous layer of sorbent-loaded composite (e.g., a web of activated carbon particles ensconced in a matrix of fibrillated PTFE such as is described in the above-mentioned U.S. Pat. No. 4,208,194) may be placed between the reflective layer and the sorbent media, to homogenize vapors permeating into the indicator or otherwise moderate the indicator response to conditions in the sorbent media.

The disclosed devices may be used for a variety of applications including organic vapor respirators, powered air purifying respirators (PAPRs), hazmat suits, collective protection filters and other applications that will be familiar to those skilled in the art.

The invention is further illustrated in the following illustrative examples, in which all parts and percentages are by weight unless otherwise indicated. The abbreviations shown below in Table 1 were employed in some of the examples:

TABLE 1

| ABBREVIATION | DESCRIPTION |
| --- | --- |
| BC | bis-catechol; 5,5',6,6'-tetrahydroxy-3,3,3',3'-tetramethyl-1,1'-spirobisindane |
| FA | fluorinated arene; tetrafluoroterephthalonitrile |
| DMF | N,N-dimethylformamide |
| THF | Tetrahydrofuran |

EXAMPLE 1

A multilayer film indicator containing an impermeable semireflective layer, a porous silica detection layer and a vapor-permeable reflective layer was prepared as follows. Glass slides were first sputter coated using a Denton Vacuum Desk II sputter coater equipped with an AuPd (60:40 Au/Pd ratio by mass) target to provide an approximately 5 nm thick semireflective layer. The sputter coating power and coating duration were 35 milliamps and 20 seconds respectively, under a vacuum of 100 millitorr. A poroussilica film was deposited onto the semireflective layer via sol-gel solution dip coating. The silica sol was prepared using a two-step hydrolysis process. In Step 1, 231.6 parts tetraethoxysilane, 195.2 parts absolute ethanol, 17.28 parts deionized water and 0.715 parts 0.07N HCl were combined in a vessel and stirred while heating at 60° C. for 90 min to form a silica sol. In Step 2, 122.97 parts of the Step 1 silica sol, 17.50 parts 0.07N HCl and 5.75 parts deionized water were combined in a beaker and stirred for 15 min. without external heating. The resulting sol-gel solution was stirred an additional 15 min while heating at 50° C., then diluted with 263.32 parts absolute ethanol. A coating solution incorporating ethyl cellulose was prepared by combining 25.25 parts of the Step 2 sol-gel solution, 25.00 parts isopropyl alcohol and 1.71 parts ETHOCEL™ Standard 20 Premium ethyl cellulose (from Dow Chemical Company) and stirring overnight (for 16 hrs) in a covered container to dissolve the ethyl cellulose completely.

The AuPd-coated glass slide was dip-coated in the coating solution using a 10 cm/min withdrawal speed, in an enclosure maintained at <30% relative humidity to prevent moisture condensation during the coating process. This applied the sol-gel coating to both sides of the slide. Because the coating was transparent it could be allowed to remain on both sides, with the coating on one side being used to make a porous detection layer and the coating on the other side residing on the eventual viewing surface. The coated sample was allowed to dry in the controlled humidity enclosure for 2 min. The coated slide was next heated in a belt furnace at 400° C. using a 30 minute heating cycle involving an 11 min heat-up time, an 8 min holding time at 400° C., and an 11 min cool down time. To ensure complete dehydration and pyrolysis of organics, the slide was reheated in an air atmosphere box furnace using a 13 hr heating cycle involving a 2 hr heat-up time to 400° C., a 1 hr holding time at 400° C., and a 10 hr cool down time to return to room temperature. The silica layer on one side of the slide was next coated with a 10 nm thick Ti tie layer and a 100 nm thick aluminum reflector layer using a CHA Industries Mark-50 evaporative coater operated at a base pressure of $1 \times 10^{-5}$ torr and No. T-2003 99.995% pure vacuum deposition grade 6 mm×6 mm pellets (from Cerac, Inc.) for the titanium layer and No. A-2049 99.99% pure vacuum deposition grade 6 mm×6 mm pellets (also from Cerac, Inc.) for the aluminum layer.

A photolithographic process with wet chemical etching was employed to make the aluminum reflective layer vapor-permeable. A hexamethyldisilazane adhesion promoter (from J. T. Baker) was spin-coated onto the aluminum layer at 2500 rpm, followed by a spin-coated layer of PR 1813 positive photoresist (from Shipley, LLC) applied at 4000 rpm to provide a 1.3 micrometer thick film. The photoresist was baked at 96° C. for 30 min, and then exposed to UV light for 9 seconds, at a UV intensity of 14 mW/cm², through a photomask over two sections of the slide. The first section employed a low etch photomask with a regular array of 3 micrometer diameter holes spaced at a 10 micrometer pitch. The second section employed a high etch photomask with a regular array of 3 micrometer holes spaced at a 5 micrometer pitch. After light exposure, the slide was dipped in MF319 developer (also from Shipley, LLC) for 45 seconds and then hardbaked at 120° C. for 30 min. The developer removed the positive photoresist in the irradiated hole regions to provide an article 50 like that shown in FIG. 5a and FIG. 5b, in which 52 designates the eventual thin film multilayer indicator, 53 designates the glass substrate through which indicator 52 will be viewed, 54 designates the Au/Pd semireflective layer, 55 designates the porous silica detection layer, 56 designates the aluminum reflective layer, and 57 designates the holes in photoresist 58.

Wet etching of the aluminum layer 56 was performed for 90 seconds at 32° C. using an acidic etch solution made by combining 500 milliliters conc. $H_3PO_4$, 19.4 milliliters conc. $HNO_3$, 96.8 milliliters conc. acetic acid, 32.2 milliliters $H_2O$ and 0.6 milliliters ethylene glycol. The etched film was immediately rinsed in deionized water. The Ti layer was next etched using a basic etch solution made by combining 100 milliliters 0.1 M EDTA, 8 milliliters conc. $NH_4OH$ and 20 milliliters 30% $H_2O_2$). The etched film was again immediately rinsed in deionized water. Finally, the remaining photoresist 58 was stripped off the aluminum layer 56 using 1165 remover (also from Shipley, LLC) to provide a completed thin film multilayer indicator 60 like that shown in FIG. 6a and FIG. 6b, in which 66 designates the vapor-permeable aluminum reflective layer and 67 designates the holes in aluminum layer 66.

EXAMPLE 2

Figure 8:
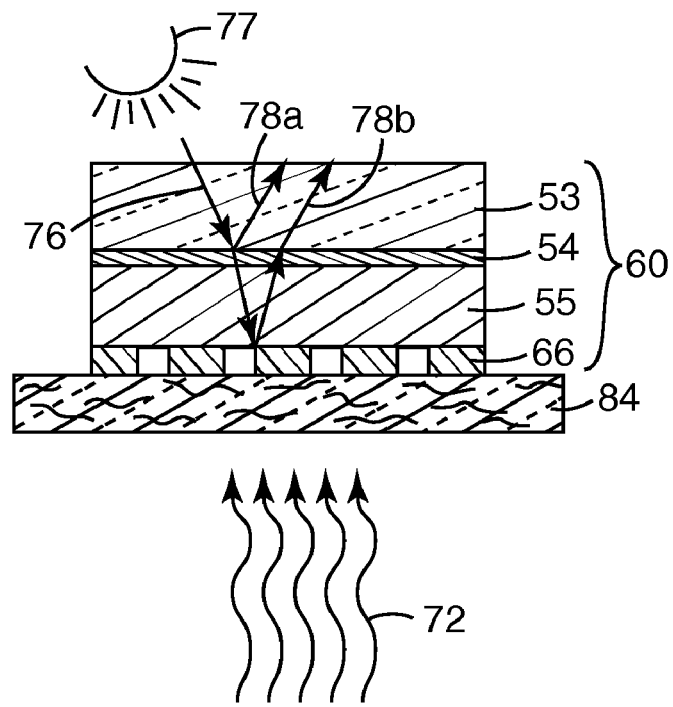
Figure 9:
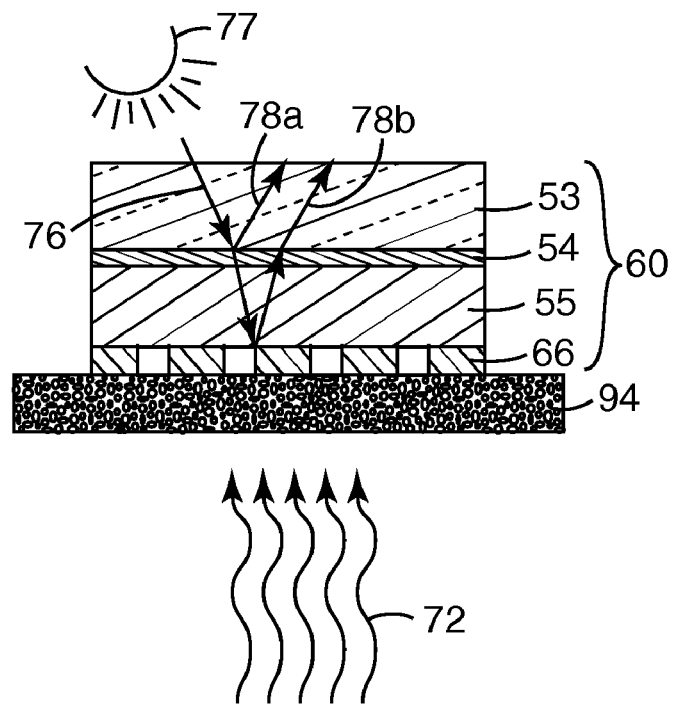
Figure 10:
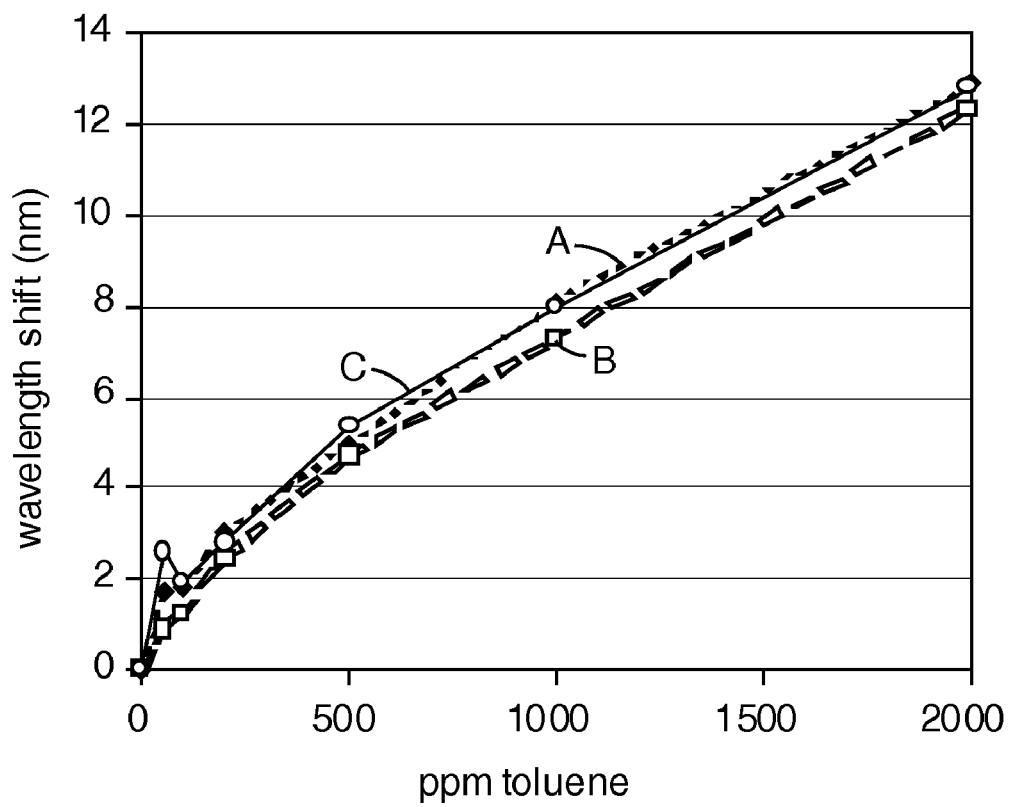
FIG. 10 through FIG. 12 are plots showing the response of various thin-film multilayer indicators to a toluene challenge.

The Example 1 thin-film indicator 60 was evaluated using three different vapor paths. The first vapor path is shown in FIG. 7. An organic vapor-containing air stream 72 flowed across indicator 60 above glass substrate 53. A small piece of woven carbon paper 74 placed against the vapor-permeable aluminum reflective layer 66 allowed a path for organic vapors in air stream 72 to reach porous silica detection layer 55. Incident light rays such as ray 76 from light source 77 were reflected by semireflective layer 54 as first reflected ray 78a and by aluminum layer 66 as second reflected ray 78b. The second vapor path is shown in FIG. 8. FIG. 8 is like FIG. 7 but the organic vapor-containing air stream 72 reached porous silica detection layer 55 through a piece of glass wool 84 placed against vapor-permeable aluminum reflective layer 66. The third vapor path is shown in FIG. 9. FIG. 9 is like FIG. 7 and FIG. 8 but the organic vapor-containing air stream 72 reached porous silica detection layer 55 through a piece of flexible microporous carbon-loaded nonwoven web 94. Web 94 contained about 500 g/m² (corresponding to an effective carbon density of about 0.22 g/cc) of 40×140 mesh activated carbon granules derived from coconut shells (from Pacific Activated Carbon Co.), dispersed throughout an elastic fibrous web made from IROGRAN™ PS 440-200 thermoplastic polyurethane (from Huntsman International LLC), prepared as described in U.S. Patent Application Publication No. US 2006/0096911 A1 (Brey et al.). The sample spectrum was monitored using a white light source, a fiber-optic reflection probe, and a spectrometer. FIG. 10 shows a plot of wavelength shift vs. ppm toluene challenge for each vapor path, with curves A, B and C respectively corresponding to the vapor paths shown in FIG. 7, FIG. 8 and FIG. 9. As shown in FIG. 10, all three vapor paths gave similar wavelength shifts at a given toluene challenge level. Curve C also shows that indicator 60 maintained its performance even when in sorptive competition with a microporous carbon-loaded web.

Figure 11:
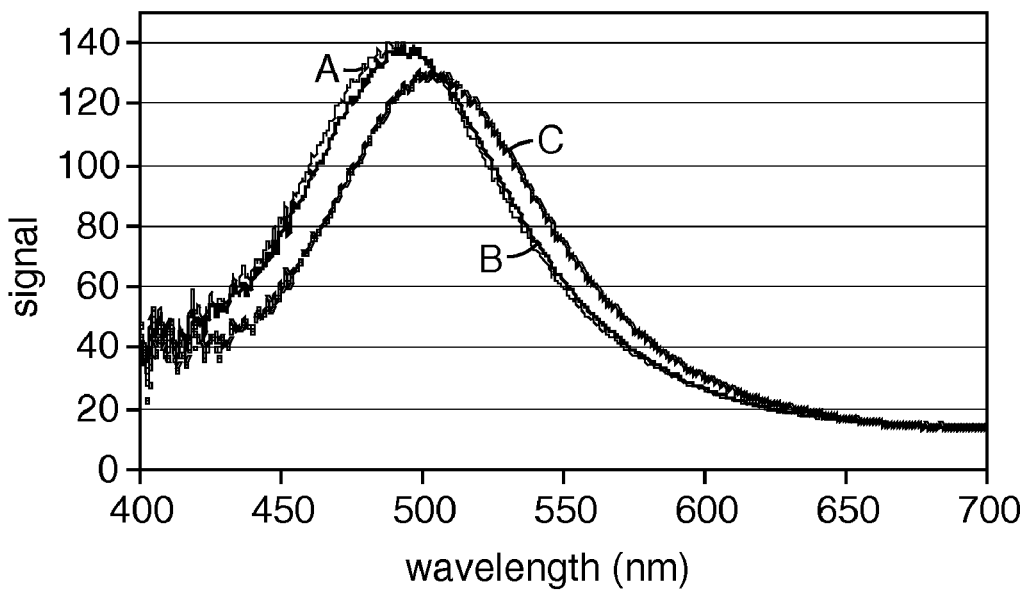
Figure 12:
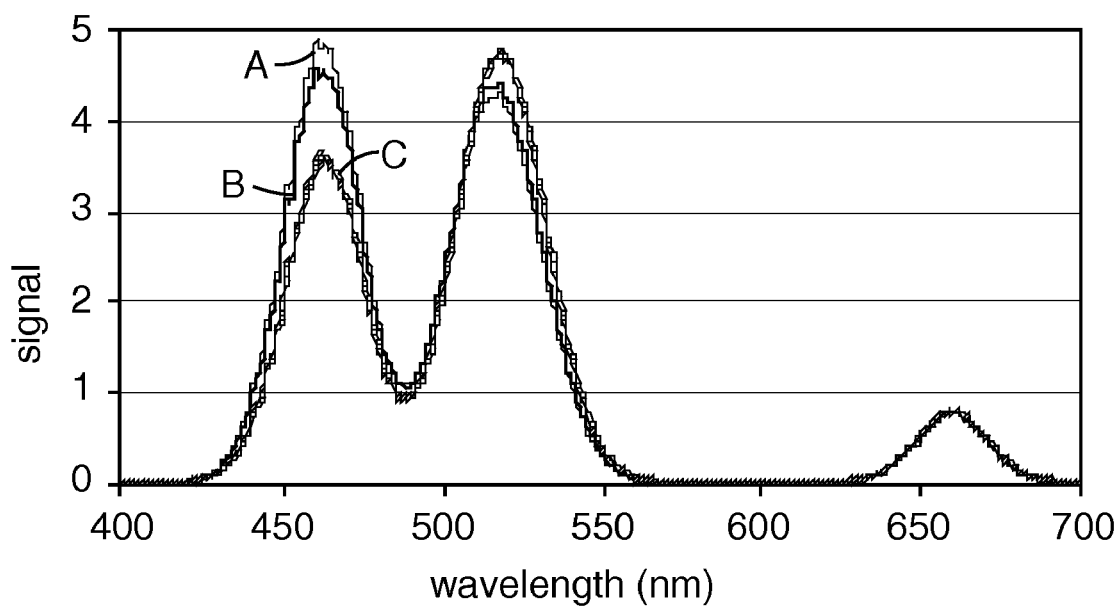

If desired, thin film indicator 60 could be illuminated using an external light source such as a light emitting diode (LED) and evaluated using a photodetector. FIG. 11 shows an acquired sample spectrum made by measuring the initial response (Curve A) of thin film indicator 60 to toluene vapor at 50 ppm (Curve B) and 2000 ppm (Curve C) toluene as a function of wavelength. FIG. 12 shows a simulation obtained by multiplying the FIG. 11 acquired sample spectrum by a Gaussian approximation of the LED spectrum, and computing the change in light intensity (in arbitrary units) measured using a suitable photodetector. The signal that would be received by a detector (e.g., a PN, PIN or avalanche photodiode with a spectral response selected to match the LED wavelength) would be determined by integrating the LED/sample spectrum. With the initial signal (Curve A in FIG. 11 and FIG. 12) normalized to 512 counts for a green LED, the detected signal for a blue LED would decrease by 21 arbitrary units at an exposure to 50 ppm toluene (Curve B in FIG. 11 and FIG. 12), indicating that an approximate 5:1 signal:noise (S/N) ratio would be obtained using standard components. The S/N ratio could be further improved by incorporating a thicker silica layer in the indicator to narrow the initial sample spectrum. Changes in the overall thin film indicator thickness may also be made to optimize the peak shift position relative to the LED spectral output. Curve C in FIG. 11 and FIG. 12 shows the predicted response at 2000 ppm toluene.

In the examples shown below, a light source and spectrometer were used to measure the change in the sensor properties. It will be appreciated however that the disclosed indicators could readily be viewed under ambient illumination.

EXAMPLE 3

A thin film indicator was prepared using polymers of intrinsic microporosity (PIMs) as the detection layer, and a laser to ablate holes in the reflective and detection layers.

PIM Polymer Preparation. PIM polymer was prepared from the monomers BC and FA generally according to the procedure reported by Budd et al. in *Advanced Materials*, 2004, Vol. 16, No. 5, pp. 456-459. 9.0 grams of BC were combined with 5.28 g of FA, 18.0 g potassium carbonate, and 120 milliliters of DMF and the mixture was reacted at 70° C. for 24 hours. The resulting polymer was dissolved in THF, precipitated three times from methanol, and then dried under vacuum at room temperature. A yellow solid product was obtained having a molecular weight (Mw) of 61,800.

Figure 13:
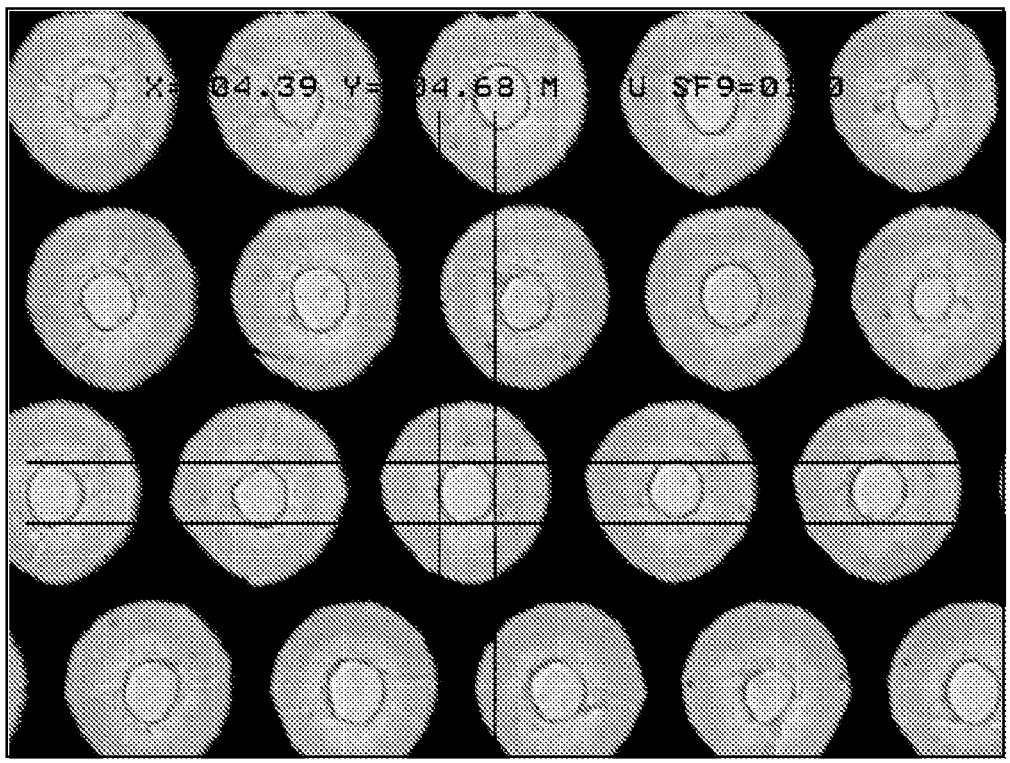
FIG. 13 is a photomicrograph of laser ablated holes through an aluminum reflective layer and polymeric detection layer.

PIM Samples with Laser processed holes. A glass slide was sputter coated with a 5 nm thick layer of Au/Pd, using a DENTON™ Vacuum Desk II sputter coater from Denton Vacuum equipped with an AuPd target with a 60:40 Au:Pd mass ratio. The sputter coating power and coating duration were 35 milliamps and 20 seconds respectively, under a vacuum of 100 millitorr. The PIM polymer was then spin-coated onto the Au/Pd layer using a 4% solution of the above-described PIM polymer in chlorobenzene coated onto the Au/Pd layer at 3,000 rpm. A 100 nm thick aluminum layer was next deposited onto the PIM polymer, using a Mark-50 evaporative coater from CHA Industries operated at a base pressure of $1 \times 10^{-5}$ torr, and 6×6 mm pellet form metal targets obtained from Cerac Inc. The sample was next laser ablated using a femtosecond machining process to create an array of conical holes through the aluminum and PIM polymer layers. The hole diameters proximate the aluminum layer were approximately 13 micrometers, and they narrowed to about 5 micrometers proximate the Au/Pd layer. A photomicrograph of the laser ablated holes (brightened so as to make the measurement data more readily visible) is shown in FIG. 13.

Figure 14:
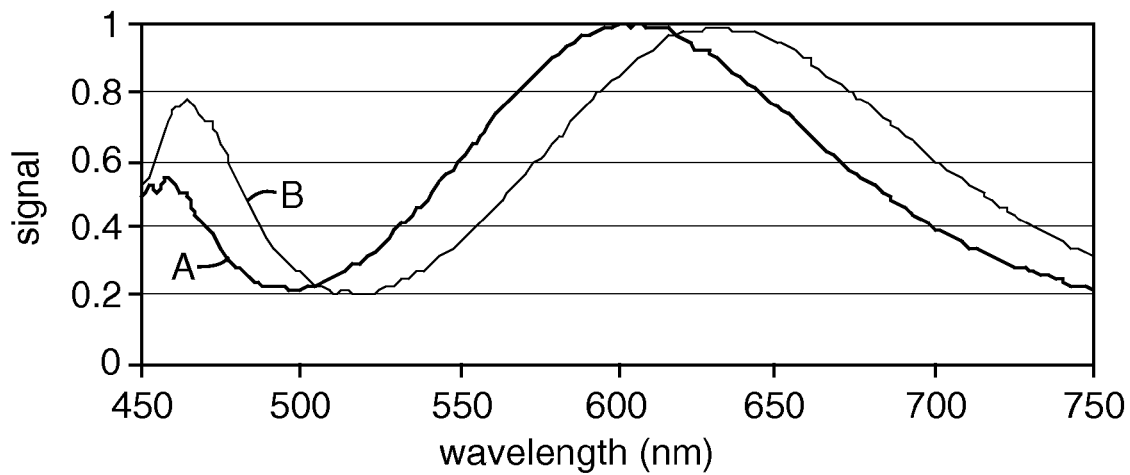
FIG. 14 through FIG. 17 are plots showing response of additional thin-film multilayer indicators to a toluene challenge.

To assess the ability of the resulting thin film indicator to compete with microporous carbon for adsorption of organic vapors, the indicator was placed upon a small piece of the Example 2 microporous carbon-loaded web, with the vapor-permeable aluminum reflective layer in contact with the web and its microporous carbon. The carbon-loaded BMF web contained 40×140 mesh activated carbon granules derived from coconut shells (from Pacific Activated Carbon Co.), dispersed throughout an elastic fibrous web made from IROGRAN™ PS 440-200 thermoplastic polyurethane (from Huntsman International LLC), prepared as described in U.S. Patent Application Publication No. US 2006/0096911 A1 (Brey et al.). The fibrous web had a 17 micrometer effective fiber diameter and a 500 $g/m^2$ carbon loading level, corresponding to about a 0.22 $g/cm^3$ carbon density. When at equilibrium with 1000 ppm of cyclohexane flowing at 32 liters/min, the carbon in this nonwoven web layer adsorbs about 0.21 g cyclohexane per g carbon. The indicator was illuminated and observed through the glass substrate using a spectrometer and fiber optic reflection probe while toluene vapor passed through the carbon-loaded layer and past the indicator. As shown in FIG. 14, where Curve A and Curve B respectively represent the initial signal and the signal at 50 ppm toluene, a peak signal wavelength shift of about 27 nm (from about 606 nm to about 633 nm) was observed. This indicated that the PIM polymer detection layer maintained its sorptive functionality when placed in thermodynamic competition with microporous carbon.

EXAMPLE 4

A thin film indicator was prepared using polymers of intrinsic microporosity (PIMs) as the detection layer, an Au/Pd semireflective layer, and a silver nanoparticle reflective layer. Using the method of Example 3, glass slides were sputter coated with a 5 nm thick layer of Au/Pd, followed by spin-coating (at 750 rpm) a layer of PIM polymer onto the Au/Pd layer. Next, two different indicators were prepared by applying a silver nanoparticle suspension to the PIM polymer layer. Indicator A was prepared using NPS-J silver nanoparticle suspension (60% in tetradecane) from Harima Corporation. Transmission Electron Microscopy (TEM) analysis of the particles revealed a size distribution of approximately 2 to 10 nm in diameter. A 0.08 g quantity of the as-received nanoparticle suspension was mixed with 2 milliliters of heptane to provide a diluted suspension containing about 3.3% silver. The diluted suspension was spin-coated onto the PIM film at 500 rpm to provide a vapor-permeable reflective layer having a reflectivity of about 62% at 500 nm relative to a 100 nm thick aluminum reference layer. Indicator B was prepared using SVE 102 silver nanoparticle suspension (30% in ethanol, 30 nm mean particle diameter) from Nippon Paint (America) Corporation. A 0.7 g quantity of this as-received suspension was mixed with 2 milliliters of ethanol to provide a diluted suspension containing about 9.1% silver. The diluted suspension was spin-coated onto the PIM film at 1000 rpm to provide a vapor-permeable reflective layer having a reflectivity of about 70% at 500 nm relative to a 100 nm thick aluminum reference layer.

Figure 15:
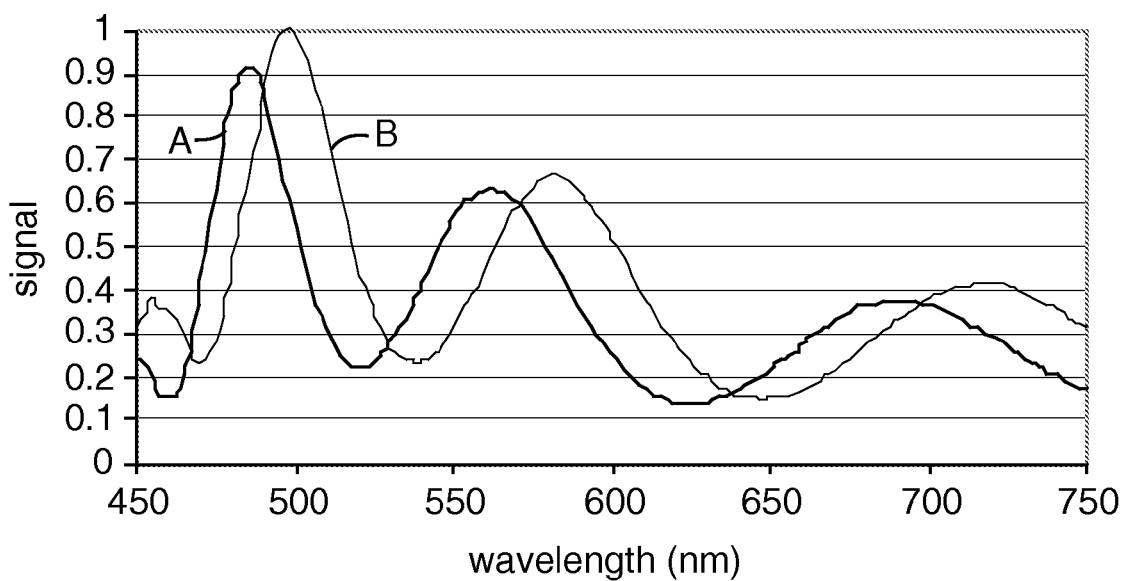
Figure 16:
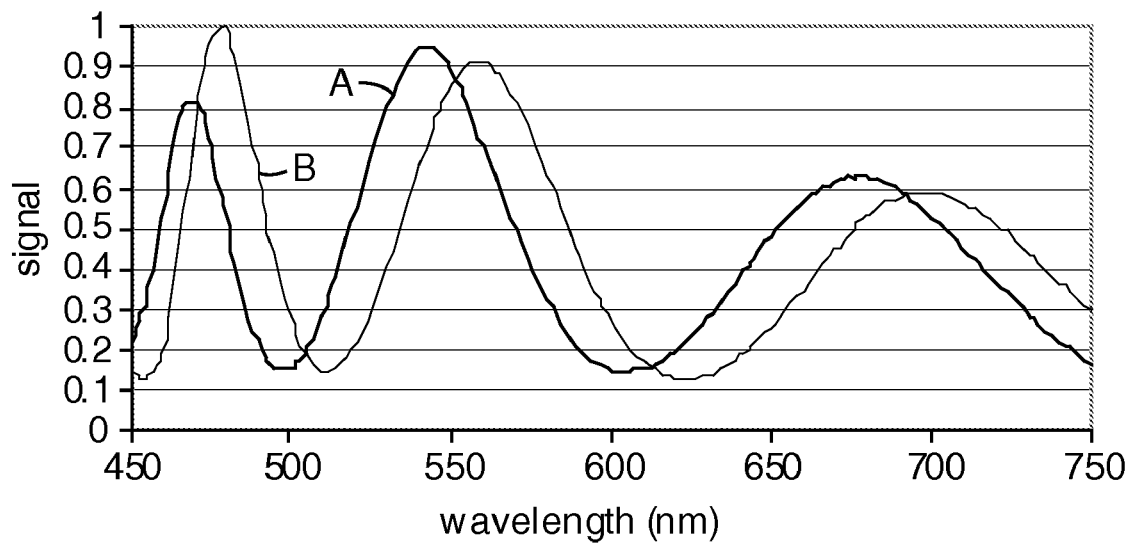

The indicators were evaluated using the method of Example 3 to assess their ability to compete with microporous carbon for adsorption of organic vapors. In FIG. 15, Curve A and Curve B respectively represent the initial signal and the signal at 50 ppm toluene for indicator A. Similarly, in FIG. 16, Curve A and Curve B respectively represent the initial signal and the signal at 50 ppm toluene for indicator B. Indicator A exhibited a peak signal wavelength shift of about 20 nm (from about 564 nm to about 584 nm) when challenged with 50 ppm toluene. Indicator B exhibited a peak signal wavelength shift of about 17 nm (from about 544 nm to about 561 nm) when challenged with 50 ppm toluene. Indicators A and B both maintained their sorptive functionality when placed in thermodynamic competition with microporous carbon.

EXAMPLE 5

Figure 17:
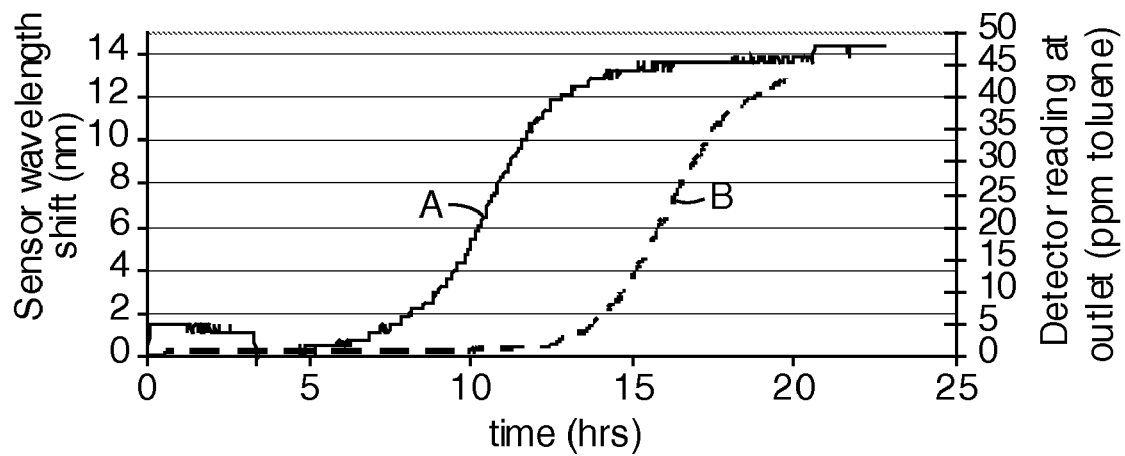

Using the method of Example 3, PIM polymer was prepared from the monomers BC and FA. Using the method of Example 3, 1 mm thick glass slides were sputter coated with a 5 nm thick layer of Au/Pd, followed by spin-coating (at 1500 rpm) a layer of PIM polymer onto the Au/Pd layer. Using the method of Example 4 (Indicator B), a diluted SVE 102 silver nanoparticle suspension was spin-coated onto the PIM film to provide a vapor-permeable nanoparticle reflective layer. The resulting thin-film indicator had a green-yellow appearance when visually observed through the glass slide. DYMAX™ No. OP-4-20641A UV-cure optical adhesive from Dymax Corporation was used to adhere the indicator to the inside sidewall of a filtration cartridge made from clear polycarbonate resin, with the vapor-permeable nanoparticle reflective layer facing the cartridge interior. The cartridge was filled with 45.7 g of activated carbon sorbent. Several small holes were drilled in the cartridge cover immediately above and upstream from the indicator to ensure adequate vapor flow at the indicator/sorbent bed interface. The cartridge was challenged using 50 ppm toluene in dry air (<3% RH) flowing at 64 liters/min. The indicator was monitored through the polycarbonate cartridge body at 50-60% of the bed depth using a fiber optic reflection probe having a <1 mm illumination spot diameter and an Ocean Optics spectrometer. Between 6 and 16 hours after the start of the toluene challenge, the indicator exhibited a gradual red-shift in coloration amounting to 14 nm in total. Taking into account the indicator's position in the cartridge, the timing and magnitude of the indicator response were consistent with separately-collected concentration data obtained using a MULTIRAE™ IR photo-ionization detector from RAE Systems Inc. positioned at the cartridge outlet. The indicator data and IR photo-ionization detector data are plotted in FIG. 17.

Figure 18:
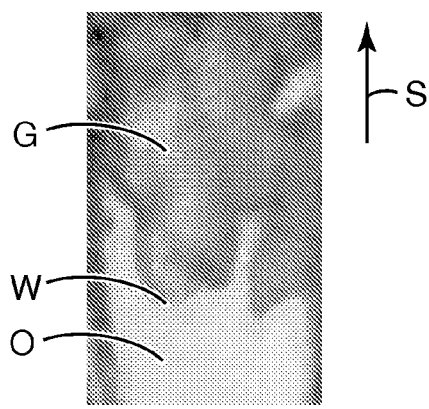
FIG. 18 and FIG. 19 are black-and-white renderings of colored wavefronts moving across thin-film multilayer indicators.

A second cartridge was assembled in the same fashion and challenged with 500 ppm styrene in dry air (<3% RH) flowing at 64 liters/min. A QX5™ computer microscope from Digital Blue Corporation was angularly adjusted so that the indicator initially appeared green when observed, and used to record the indicator's appearance when challenged with styrene vapor. As the challenge progressed, the indicator's initial green coloration changed to orange along a color change front that moved from the cartridge inlet towards its outlet. An RGB histogram of the initial green coloration returned mean values of r=145, g=191, and b=121. After the indicator responded to the styrene vapor by changing green to orange, the histogram values were r=208, g=179, and b=127. FIG. 18 shows a black and white rendering of the indicator coloration part-way through the experiment and illustrates the vapor wavefront progression and appearance. The green and orange visible portions are identified with the letters G and O, the wavefront is identified with the letter W and the styrene flow direction is identified with the letter S.

EXAMPLE 6

Figure 19:

Using the method of Example 3, PIM polymer was prepared from the monomers BC and FA. Using a CHA Industries Mark-50 evaporator operated at a base pressure of $1 \times 10^{-5}$ torr and No. T-2003 titanium pellets (99.995% purity, 6×6 mm, from Cerac Inc.), cleaned glass slides were metallized with a 10 nm thick semireflective Ti layer. A 4% solution of the PIM polymer in chlorobenzene was spin-coated onto the Ti layer at 1000 rpm. Using the method of Example 4 (Indicator B), a diluted SVE 102 silver nanoparticle suspension was spin-coated onto the PIM film to provide a vapor-permeable reflective layer. Following silver deposition, the film sample was heated at 150° C. in air for 1 hour. The resulting thin-film indicator had a green appearance when visually observed through the glass slide. DYMAX™ No. OP-4-20641A UV-cure optical adhesive was used to adhere the indicator to an additional glass slide layer. The resulting glass slide stack was adhered to the inner sidewall of a filtration cartridge made from clear polycarbonate plastic. Next, using a method like that described in U.S. Pat. No. 4,153,661 (Ree et al.) and Example 1 of U.S. Pat. No. 4,208,194, a dough was formed by combining an aqueous polytetrafluoroethylene ("PTFE") particle dispersion with finely ground, activated carbon particles. The dough was milled and dried but not calendared to provide a composite web of activated carbon particles ensconced in a matrix of fibrillated PTFE. A layer of the carbon composite web was attached to the top edge of the glass slide stack and folded down to cover the porous nanoparticle reflective layer. The remaining filtration cartridge volume was then filled with 45.8 g of activated carbon sorbent. Several small holes were drilled in the cartridge cover immediately above and upstream from the indicator to ensure adequate vapor flow at the indicator/sorbent bed interface. The cartridge was challenged with 200 ppm styrene in dry air (<3% RH) at a 32 liters/min flowrate. Using ambient lighting, a TRENDnet™ Model TV-IP201W wireless camera (from TRENDnet Company) was angularly adjusted so that the indicator initially appeared green when observed, and used to record the indicator's appearance when challenged with styrene vapor. As the experiment progressed, the indicator color changed from the initial green color to deep red, with the color change appearing first near the filtration cartridge inlet and moving towards the cartridge outlet. When the vapor flow was stopped, the wavefront blurred slightly but did not move closer to or farther from the cartridge outlet. An RGB histogram of the initial green color returned mean values of r=30, g=99, and b=51. After the indicator responded to the styrene vapor by changing green to red, the histogram values were r=97, g=56, and b=66. FIG. 19 shows a black and white rendering of the indicator coloration part-way through the experiment and illustrates the vapor wavefront progression and appearance. The carbon sorbent is identified with the letter C, the green and red visible indicator portions are identified with the letters G and R, the wavefront is identified with the letter W and the styrene flow direction is identified with the letter S. The wavefront was noticeably more uniform than the wavefront in FIG. 18, which involved a filtration cartridge that did not include a carbon composite web between the indicator and the sorbent media.

EXAMPLE 7

Using the method of Example 6, a 10 nm thick titanium semireflective layer was evaporatively coated onto a cleaned glass slide. The Ti-coated glass slide was next mounted onto a planar electrode. The electrode was in turn mounted in an aluminum vacuum chamber equipped with turbomolecular pump in series with a Roots blower and a dry mechanical pump. The chamber was closed and pumped down to a base pressure of 0.0005 Torr. A mixture of tetramethylsilane, oxygen and butadiene gases was introduced into the chamber at respective flow rates of 100 standard cubic centimeters per minute (sccm), 100 sccm and 160 sccm. A plasma was formed by powering the planar electrode using a Model RF50S radio frequency power supply (from RF Power Products) operating through a Model AMN3000 impedance matching network (from PlasmaTherm Inc.). While the plasma was in operation the delivered power was maintained at 75 watts and the chamber pressure was maintained at 37 mTorr. Deposition was carried out for 14 minutes to yield a plasma-deposited thin organic film having a 0.768 micrometer thickness. The plasma-deposited thin film was annealed in a vacuum furnace at a temperature of 450° C. for 1 hour to provide a microporous thin film detection layer atop the titanium semireflective layer. A 0.0475 g quantity of SILVER NANOINK™ silver nanoparticle slurry in methanol (Lot S Ag 031027W, from Advanced Nano Products Co., Ltd, Korea) was diluted with an additional 2 milliliters of methanol to provide a dilute suspension which was spin-coated onto the thin film detection layer at 1500 rpm. The resulting spin-coated silver nanoparticle layer was allowed to dry, yielding a vapor-permeable thin film silver nanoparticle reflective layer atop the thin film detection layer.

Figure 20:
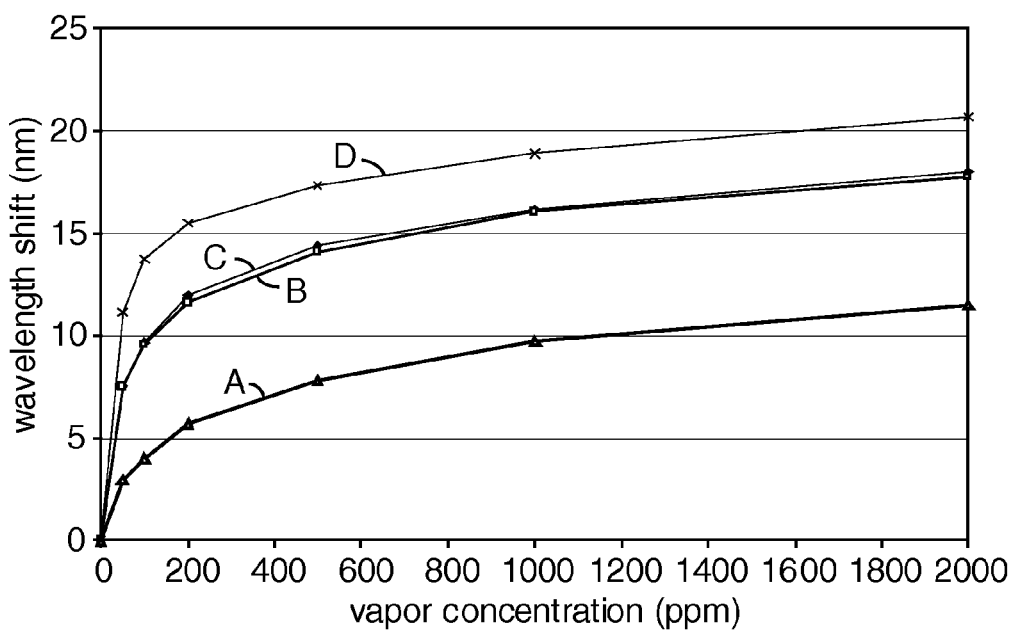
FIG. 20 is a plot showing the response of a thin-film multilayer indicator to challenges from several vapors.

To assess the ability of the resulting indicator to compete with microporous carbon for adsorption of organic vapors, the indicator was placed upon a small piece of the carbon composite web employed in Example 6, with the permeable reflective layer in contact with the carbon composite web. The indicator appearance was observed through the glass substrate using a spectrometer and fiber optic reflection probe to evaluate the sensor coloration. The sensor was exposed to toluene, methyl ethyl ketone and ethylbenzene vapor streams passing through the carbon composite web. The toluene and methyl ethyl ketone streams were maintained at less than 5% relative humidity and the ethylbenzene stream was maintained at 82% relative humidity. The results are shown in FIG. 20, where Curves A, C and D respectively show the methyl ethyl ketone, toluene and ethylbenzene vapor concentration vs. the observed wavelength shift, and where Curve B shows the toluene vapor concentration vs. the observed wavelength shift when the carbon composite web was not employed. The results in FIG. 20 show that the disclosed indicator exhibited wavelength shifts of about 6 to 16 nm at a 200 ppm vapor concentration, and wavelength shifts of about 12 to 21 nm at a 2000 ppm vapor concentration. Curves B and C also show that the porous detection layer in the disclosed indicator maintained its sorptive capability even when placed in thermodynamic competition with microporous carbon.

EXAMPLE 8

Using the method of Example 3, PIM polymer was prepared from the monomers BC and FA. Using a CHA Industries Mark-50 evaporator operated at a base pressure of $1 \times 10^{-5}$ torr and No. T-2003 titanium pellets, cleaned glass slides were metallized with a 10 nm thick semireflective layer of Ti. A 4% solution of the PIM polymer in chlorobenzene was spin-coated onto the Ti layer at 2000 rpm. Using the method of Example 4 (Indicator B), a diluted SVE 102 silver nanoparticle suspension was spin-coated onto the PIM film and dried under vacuum at room temperature for 12 hours to provide a multilayer thin-film indicator with a PIM detection layer located between a titanium semireflective layer and a vapor-permeable metal nanoparticle reflective layer. The indicator had a green appearance when visually observed through the glass slide and semireflective layer.

To assess the ability of the indicator to compete with microporous carbon for adsorption of organic vapors, the indicator was placed upon a small piece of the carbon-loaded nonwoven web 94 used in Example 2. At equilibrium with 1000 ppm of cyclohexane flowing at 32 liters/min, the carbon in the layer adsorbs 0.21 g cyclohexane per gram of carbon. The indicator appearance was observed through the glass substrate using a spectrometer and fiber optic reflection probe, and measured in dry air (<3% RH) and at 85% relative humidity. The indicator exhibited only a 3 nm spectral shift at 85% relative humidity compared to the results in dry air, thus demonstrating that the indicator was generally insensitive to high humidity conditions. Next, while maintaining an 85% relative humidity atmosphere, the carbon-loaded nonwoven web was exposed to styrene vapor at 20 ppm. The indicator exhibited a 23 nm spectral shift, demonstrating that the indicator maintained its sorptive functionality when placed in thermodynamic competition with microporous carbon exposed to a humid analyte stream.

EXAMPLE 9

Using the method of Example 6, a 10 nm thick titanium semireflective layer was evaporatively coated onto two cleaned glass slides. PIM polymer with a weight average molecular weight (Mw) of 62,900 was prepared using the method of Example 3 and the monomers BC and FA. A 3.2% solution of the PIM polymer in a 60/40 chlorobenzene/tetrahydropyran mixture was spin-coated onto the Ti layers of the coated glass slides at 1000 rpm. A 1.0 g quantity of SILVERJET™ DGP 40LT-25C silver nanoparticles (43.25% in methanol, from Advanced Nano Products Co., Ltd., Korea) was added to 2 milliliters methanol to give a diluted suspension containing 16.8% solids. The diluted suspension was spincoated at 600 rpm onto the PIM layer on each coated slide. One slide was then air dried and identified as indicator A. The other slide was heated at 150° C. for 1 hour in air to partially sinter the silver particles and identified as indicator B. Indicator B had a reflectivity of about 39% at 500 nm relative to a 100 nm thick aluminum reference layer.

To assess the abilities of both indicators to compete with microporous carbon for adsorption of organic vapors, the coated side of each slide was placed against a small piece of the carbon-loaded web 94 used in Example 2, with the permeable nanoparticle reflector in contact with the carbon-loaded web. The indicators were observed through the glass substrate and semireflective layer using a spectrometer and fiber optic reflection probe. The indicators were exposed to a 50 ppm toluene vapor stream passing through the carbon-loaded web. The spectral peak for Indicator A shifted from 532 nm to 558 nm, and the spectral minimum for Indicator B shifted from 609 nm to 629 nm, demonstrating that in each instance the indicator maintained sorptive functionality when placed in thermodynamic competition with microporous carbon.

All patents and patent applications cited above, including those in the Background section, are incorporated by reference into this document in total. To the extent that there is a conflict, this document will prevail.

A number of embodiments of the invention have been described. Nevertheless, it will be understood that various modifications may be made without departing from the invention. Accordingly, other embodiments are within the scope of the following claims.

We claim:

1. A protective device that comprises an enclosure including a gas inlet, gas outlet and a thin-film multilayer indicator, wherein:
   A) the enclosure contains sorbent media that can sorb a vapor of interest flowing from the inlet towards the outlet;
   B) the thin-film multilayer indicator comprises:
      i) a porous detection layer whose optical thickness changes in the presence of the vapor, located between
      ii) a semireflective layer viewable from outside the enclosure and iii) a reflective layer that contains metal particles and that is permeable to the vapor; and C) the reflective layer is in sufficient proximity to the media such that with equilibration at the applied vapor concentration between at least a portion of the media and the vapor, the vapor can pass from the media through the reflective layer and into the detection layer and change the detection layer optical thickness sufficiently to cause a visibly discernible change in the indicator appearance as viewed through the semireflective layer.

2. A device according to claim 1 wherein interference coloration is created or destroyed within the indicator when in the presence of the vapor.

3. A device according to claim 2 wherein the indicator provides a colorimetric change in appearance without requiring a powered light source, optical detector or spectral analyzer.

4. A device according to claim 1 wherein the indicator is illuminated using an external light source and evaluated using a photodetector.

5. A device according to claim 1 wherein a color change front advances with the flow of vapor through the media past the indicator.

6. A device according to claim 1 wherein the device comprises an air purifying respirator cartridge.

7. A device according to claim 1 comprising an array of indicators traversing the vapor flow path.

8. A device according to claim 1 wherein the indicator is flexible and sufficiently bendable without fracturing so that it can be made using one or more roll processing steps.

9. A device according to claim 1 wherein the indicator further comprises a substrate.

10. A device according to claim 9 wherein the enclosure comprises a transparent viewing port over the indicator.

11. A device according to claim 1 wherein the media comprises a finely-divided solid.

12. A device according to claim 11 wherein the media comprises carbon.

13. A device according to claim 1 wherein the detection layer has a range of pore sizes or a surface area selected to provide vapor sorption characteristics like those of the media.

14. A device according to claim 13 wherein the indicator has a visibly discernable coloration and the detection layer has pore diameters smaller than the indicator coloration peak wavelength.

15. A device according to claim 1 wherein the detection layer comprises porous silica, metal oxide, metal nitride, metal oxynitride or other inorganic material that can be formed into transparent and porous layers of appropriate thickness for producing color or a colorimetric change by optical interference.

16. A device according to claim 1 wherein the detection layer has been formed by plasma-activated chemical vapor deposition.

17. A device according to claim 1 wherein the detection layer comprises a polymer, copolymer or mixture thereof prepared or preparable from a hydrophobic (meth)acrylate, difunctional monomer, vinyl monomer, hydrocarbon monomer (olefin), silane monomer, fluorinated monomer, hydroxylated monomers, acrylamide, anhydride, aldehyde-functionalized monomer, amine- or amine salt-functionalized monomer, acid-functionalized monomer, epoxide-functionalized monomer or mixture or combination thereof.

18. A device according to claim 1 wherein the detection layer comprises a polymer having intrinsic microporosity.

19. A device according to claim 18 wherein the detection layer comprises a polymer of bis-catechol and a fluorinated arene.

20. A device according to claim 1 wherein the semireflective and reflective layers comprise a metal or metal oxide or a multilayer optical film.

21. A device according to claim 1 wherein the face of the semireflective layer adjacent the detection layer is flat to within about±10 nm.

22. A device according to claim 1 further comprising a porous layer of sorbent-loaded composite between the reflective layer and a bed of sorbent media.

23. A respirator comprising a device according to claim 1.

24. The protective device of claim 1, wherein the metal particles are partially sintered.

25. The protective device of claim 24, wherein the metal particles comprise silver.

26. The protective device of claim 1, wherein the metal particles comprise a nanoparticle layer that is at least 2 or more nanoparticles thick.

27. The protective device of claim 1 being a filter cartridge.

28. The protective device of claim 1 being a respirator that includes one or more filter cartridges.

29. A process for making a protective device, which process comprises:

A) providing an enclosure including:
  i) a space for containing sorbent media that will sorb a vapor of interest flowing through the enclosure; and
  ii) a thin-film multilayer indicator comprising:
    a) a porous detection layer whose optical thickness will change in the presence of the vapor, located between
    b) a semireflective layer viewable from outside the enclosure and
    c) a reflective layer that contains metal particles and that is permeable to the vapor;

B) placing the media in the enclosure in sufficient proximity to the reflective layer such that upon saturation of at least a portion of the media by the vapor, vapor can pass through the reflective layer into the detection layer and change the detection layer optical thickness sufficiently to cause a visibly discernible change in the indicator appearance as viewed through the semireflective layer; and C) sealing the enclosure.

30. A process according to claim 29 wherein the device comprises an air purifying respirator cartridge.

31. A process according to claim 29 wherein the indicator is flexible and bendable without fracturing.

32. A process according to claim 29 wherein the enclosure comprises a transparent viewing port over the indicator.

33. A process according to claim 29 wherein the media comprises a finely-divided solid.

34. A process according to claim 33 wherein the media comprises carbon.

35. A process according to claim 29 wherein the detection layer comprises porous silica, metal oxide, metal nitride, metal oxynitride or other inorganic material that can be formed into transparent and porous layers of appropriate thickness for producing color or a colorimetric change by optical interference.

36. A process according to claim 29 further comprising forming the detection layer by plasma-activated chemical vapor deposition.

37. A process according to claim 29 wherein the detection layer comprises a polymer, copolymer or mixture thereof prepared or preparable from a hydrophobic (meth)acrylate, difunctional monomer, vinyl monomer, hydrocarbon monomer (olefin), silane monomer, fluorinated monomer, hydroxylated monomers, acrylamide, anhydride, aldehyde-functionalized monomer, amine- or amine salt-functionalized monomer, acid-functionalized monomer, epoxide-functionalized monomer or mixture or combination thereof.

38. A process according to claim 29 wherein the detection layer comprises a polymer having intrinsic microporosity.

39. A process according to claim 38 wherein the detection layer comprises a polymer of bis-catechol and a fluorinated arene.

40. A process according to claim 29 wherein the semireflective and reflective layers comprise a metal or metal oxide or a multilayer optical film.

41. A process according to claim 29 wherein the face of the semireflective layer adjacent the detection layer is flat to within about ±10 nm.

42. A process according to claim 29 further comprising placing a porous layer of sorbent-loaded composite between the reflective layer and a bed of sorbent media.

43. A process according to claim 29 further comprising attaching the enclosure to a respirator.

44. A method of making a filter cartridge, which method comprises:

A) providing an enclosure including:
  i) a space for containing sorbent media that will sorb a vapor of interest flowing through the enclosure; and
  ii) a thin-film multilayer indicator comprising:
    a) a porous detection layer whose optical thickness will change in the presence of the vapor, located between
    b) a semireflective layer viewable from outside the enclosure and
    c) a reflective layer that contains metal nanoparticles and that is permeable to the vapor;
B) placing the media in the enclosure in sufficient proximity to the reflective layer such that upon saturation of at least a portion of the media by the vapor, vapor can pass through the reflective layer into the detection layer and change the detection layer optical thickness sufficiently to cause a visibly discernible change in the indicator appearance as viewed through the semireflective layer; and
C) sealing the enclosure.

* * * * *

UNITED STATES PATENT AND TRADEMARK OFFICE
CERTIFICATE OF CORRECTION

| | | |
|---|---|---|
| PATENT NO. | : 8,067,110 B2 | Page 1 of 1 |
| APPLICATION NO. | : 11/530614 | |
| DATED | : November 29, 2011 | |
| INVENTOR(S) | : Neal A Rakow | |

It is certified that error appears in the above-identified patent and that said Letters Patent is hereby corrected as shown below:

Column 2
Line 34, delete "calorimetric" and insert -- colorimetric --, therefor.
Lines 39-40, delete "calorimetric" and insert -- colorimetric --, therefor.

Column 8
Line 18, delete "calorimetric" and insert -- colorimetric --, therefor.
Line 43, delete "calorimetric" and insert -- colorimetric --, therefor.

Signed and Sealed this
Fourteenth Day of February, 2012

David J. Kappos
*Director of the United States Patent and Trademark Office*